United States Patent [19]

Daly et al.

[11] Patent Number: 5,019,506
[45] Date of Patent: May 28, 1991

[54] PLASMID AND USES THEREOF

[75] Inventors: Charles Daly; Gerald F. Fitzgerald, both of Cork; Aidan Coffey, Waterford; Veronica A. Costello, Kerry; Maeve C. Murphy, Wexford, all of Ireland; Andreas Baumgartner, Bern, Switzerland

[73] Assignee: University College, Cork, Cork, Ireland

[21] Appl. No.: 242,259

[22] Filed: Sep. 8, 1988

Related U.S. Application Data

[63] Continuation-in-part of Ser. No. 52,343, May 21, 1987, abandoned.

[30] Foreign Application Priority Data

May 21, 1986 [IE] Ireland ................................ 1352/86
Sep. 17, 1987 [IE] Ireland ................................ 2518/87

[51] Int. Cl.$^5$ .................... C12N 15/00; C12N 1/20
[52] U.S. Cl. ............................ 435/172.3; 435/252.3; 435/252.4; 435/320.1
[58] Field of Search ................ 536/27; 435/320, 253, 435/252.3, 253.4, 172.3; 935/27, 56, 74, 79, 106, 6, 72

[56] References Cited

FOREIGN PATENT DOCUMENTS 0208468 1/1987 European Pat. Off. .

OTHER PUBLICATIONS

Klaenhammer, T. R. and R. B. Sanozky, *Conjugal Transfer from Streptococcus Lactis ME2 of Plasmids Encoding Phage Resistance, Nisin Resistance and Lactose-Fermenting Ability: Evidence for a High-frequency Conjugative Plasmid Responsible for Abortive Infection of Virulent Bacteriophage*, Journal of General Microbiology (1985), 131, pp. 1531–1541.

Steenson, L. R. and T. B. Klaenhammer, *Streptococcus Cremoris M12R Transconjugants Carrying the Conjugal Plasmid pTR2030 are Insensitive to Attack by Lytic Bacteriophages*, Applied and Environmental Microbiology, Oct. 1985, vol. 50, No. 4, pp. 851–858.

Sing, W. D. and T. R. Klaenhammer, *Conjugal Transfer of Bacteriophage Resistance Determinants on pTR2030 into Streptococcus cremoris Strains*, Applied and Environmental Microbiology, Jun. 1986, vol. 51, No. 6, pp. 1264–1271.

de Vos et al., *FEMS Microbiol. Lett.* 23:175–178, 1984.

Jarvis, A. W. and T. R. Klaenhammer, *Bacteriophage Resistance Conferred on Lactic Steptococci by the Conjugative Plasmid pTR2030: Effects on Small Isometric-, Large Isometric-, and Prolate-Headed Phages*. Applied and Environmental Microbiology, Jun. 1986, vol. 51, No. 6, pp. 1272–1277.

Jarvis, A. W. and T. R. Klaenhammer, *Bacteriophage Resistance Plasmid pTR2030 Inhibits Lytic Infection $r_1t$ Temperate Bacteriophage but Not Induction of $r_1t$ Prophage in Streptococcus Cremoris R1*. Applied and Environmental Microbiology, Feb. 1987, vol. 53, No. 2, pp. 385–389.

Sanders, M. E., P. J. Leonhard, W. D. Sing and T. R. Klaenhammer, *Conjugal Strategy for Construction of Fast Acid-Producing, Bacteriophage-Resistant Lactic Streptococci for Use in Dairy Fermentations.* Applied and Environmental Microbiology, Nov. 1986, vol. 52, No. 5, pp. 1001–1007.

*Primary Examiner*—Robin L. Teskin
*Assistant Examiner*—Beth A. Burrous
*Attorney, Agent, or Firm*—Wegner, Cantor, Mueller & Player

[57] ABSTRACT

Plasmids carrying one or more genes which confer phage insensitivity upon *Streptococcus lactis* or *Streptococcus lactis* subsp. diacetylactis as well as *Streptococcus cremoris* bacteria in which the insensitivity is not destroyed at temperatures of up to 40° C. are described. DNA fragments are also described which encode phage insensitivity. Such plasmids and DNA fragments are suitable for conferring phage insensitivity upon bacteria or food starter cultures containing bacteria.

6 Claims, 20 Drawing Sheets

PLASMID AND USES THEREOF

This application is a continuation-in-part of U.S. patent application Ser. No. 052,343 filed 21st May 1987, now abandoned.

FIELD OF THE INVENTION

This invention relates to plasmids and DNA fragments which confer phage insensitivity on bacteria, particularly lactic acid bacteria, bacteria to which such plasmids or DNA fragments have been introduced and use of such plasmids or DNA fragments in the food industry, particularly the dairy industry.

It is known that the activity of a starter culture in dairy fermentations such as the production of cheese, cultured buttermilk, cultured butter or sour cream can be adversely affected by bacteriophage attack. It is accepted that there is an urgent need to extend the range of commercially stable phage-insensitive strains available to the dairy industry. Genetic studies on the lactic streptococci have suggested that genetic manipulation may be used to construct strains with new and/or improved industrial traits. The term "phage insensitivity" and "phage insensitive" are used throughout this application to denote an inability of a bacteriophage to propagate on a host strain. The term "resistance" is commonly used in the lactic streptococcal/bacteriophage literature to describe hosts which do not allow phage propagation even though the "resistance" mechanism is not known, although in a strict scientific sense the term "resistance" implies an inability of a phage to adsorb to a host.

BACKGROUND OF THE INVENTION

A number of plasmid-encoded mechanisms involved in host-mediated insensitivity to phage attack in the lactic streptococci have been described in the literature. The insensitivity may be at the level of adsorption, restriction-modification (R-M) of phage DNA, or by powerful, but as yet uncharacterized, mechanisms that prevent phage maturation.

Two plasmid-encoded adsorption blocking systems have been described by Sanders and Klaenhammer (19) and de Vos et al (20). These molecules, pME0030 (30 Mdal. from S. lactis ME2, ref. 19) and pSKI12 (34 Mdal, from S. cremoris SKII, ref. 20) have the effect of significantly inhibiting phage adsorption to plasmid-containing hosts with a consequent suppression of phage replication. Elimination of the plasmids from their respective hosts results in highly efficient phage adsorption and an increased sensitivity to specific phage. However, since neither plasmid was reported to be conjugative, it may be difficult to exploit them to construct new phage insensitive starter culture strains.

Plasmids encoding R-M activity, some of which are conjugative, occur widely in lactic streptococci (21, 22, 23, 24, 25, 26, 27, 28). Although powerful R-M systems have been achieved by the additive effect of two plasmids (21, 24) the potential of R-M as a defence mechanism against phage is limited since the insensitivity conferred is not complete and phage which become modified (i.e. protected from subsequent restriction) pose a threat to the host that previously restricted the unmodified phage.

A plasmid pNP40 originating in Streotococcus lactis subsp. diacetvlactis DRC3 has been described by McKay L. L. and Baldwin K. A. (1). The mechanism associated with this plasmid was effective at 21° and 32° C. but not at 37° C. Furthermore, evidence was presented that pNP40 was thermosensitive in its replication. Klaenhammer et. al. have described a plasmid pTR2030, originating in S. lactis ME2, which encodes a heat-sensitive phage-defence mechanism which limits the burst size and plaque size of specific phage without altering the efficiency of plaquing (e.o.p.) or the level of adsorption (2). This plasmid is described in European Specification No. 0208468A2. The pTR2030 mechanism was heat sensitive in an S. lactis background but not in S. cremoris hosts when challenged with isometric-headed phage (2, 3). The effect of high temperature on the activity of the pTR2030 associated mechanism against prolate-headed phage was not assessed. pTR2030 could be conjugally transferred to a range of S. cremoris strains (3, 4) and it was established that the plasmid conferred resistance to small isometric-headed phage. However, prolate- and large isometric-headed phage were either not inhibited in the transconjugants or exhibited a reduction in plaque size without a reduction in e.o.p. (5). The presence of pTR2030 in a lysogen was shown to be unable to inhibit prophage induction in S. cremoris R1 but it did prevent the lysogenic phage from infecting a pTR2030-containing prophage cured derivative S. cremoris R1 (6). It was suggested that the phage resistance mechanism acts at the cell surface or membrane to prevent small isometric-headed phage DNA passage into the host cell or inhibits early events required for lytic replication of externally infecting phage (6). Sanders et al. have devised a conjugal strategy for the construction of fast acid-producing, bacteriophage-resistant lactic streptococci for use in dairy fermentations by introducing pTR2030 into lactose-utilising, antibiotic-sensitive recipient strains (7). This report also describes the use of deletion analysis to locate the region of pTR2030 encoding phage resistance and the cloning of a specific HindIII fragment in E. coli using the pBR322 vector plasmid. A 150 bp region of pTR2030 was sequenced and 19 base pairs from within this region were chemically synthesized to be used as a very specific probe to identify strains harbouring pTR2030.

Reference 4, 5, 6 and 7 and European Specification No. 0208468A2 were published after the first priority date of the present application.

Although there has been considerable progress in the study of plasmid-encoded phage insensitivity mechanisms, there is still a definite need for more potent systems. In particular, a heat insensitive mechanism active against virulent prolate-headed phage in S. cremoris and S. lactis backgrounds is highly desirable for use in the food industry.

It is an object of the present invention to provide plasmids or DNA fragments which encode phage-insensitivity in species useful in cheese manufacture and other areas of the food industry.

SUMMARY OF THE INVENTION

The invention provides a plasmid carrying one or more genes which confer phage insensitivity upon Streptococcus lactis or Streptococcus lactis subsp. diacetylactis as well as Streptococcus cremoris bacteria wherein the said phage insensitivity is not destroyed by temperatures of up to 40° C.

The plasmids of the present invention are isolated plasmids.

The term "isolated plasmid" as used herein means a plasmid which has been removed from the original host in which it was identified, and progeny and derivatives thereof, having the same phage insensitivity properties thereof, and includes such plasmids both when in a bacterium-free state and when they have been introduced into another bacterial cell.

In particular the invention provides a plasmid as defined above originating in a *Streptococcus cremoris* or a *Streptococcus lactis* strain, and a plasmid which confers insensitivity to both small isometric-headed and prolate-headed phage.

The invention further provides a recombinant plasmid carrying genes which encode phage insensitivity and lactose utilization in lactic streptococci, such a plasmid being generated by in vivo cloning.

The invention also provides a recombinant plasmid carrying genes which encode phage insensitivity, lactose utilization and high-frequency conjugative ability in lactic streptococci, such a plasmid being generated by in vivo cloning.

In particular aspects, the invention provides plasmids
pCI750
pCI777
pCI829
pCI528
isogenic derivatives thereof; plasmids which are substantially similar thereto, particularly plasmids having at least about 80% homology therewith; and DNA in such plasmids encoding phage insensitivity with or without lactose utilization and with or without high frequency conjugative ability.

In another aspect the invention provides DNA fragments which confer phage insensitivity on Streotococcus species. In particular the DNA fragment confers phage insensitivity on *S. lactis*. The invention provides DNA fragments which confer insensitivity to small isometricheaded phage and partial insensitivity to prolate-headed phage.

More particularly, the fragment may be a 4 kilo base (kb) BglII fragment derived from the plasmid pCI829 as deposited in *S. lactis* AC001 at the National Collection of Industrial Bacteria (NCIB). Aberdeen, Scotland, under the accession number 12263 on 16th May 1986, or a 6.3 kb StuI fragment also derived from pCI829 and having the restriction map:

which is substantially similar thereto or which has at least about 80% homology therewith.

The invention also provides a plasmid comprising any of the DNA fragments as defined above.

The invention also provides methods of conferring phage insensitivity on a bacterium comprising introducing into the said bacterium a DNA fragment or a plasmid as defined above.

The invention also provides bacterial hosts, particularly lactic streptococcal hosts into which has(ve) been introduced one or more of the plasmids or DNA fragments defined above; more particularly a host into which has been introduced two of the plasmids defined above whose effect on the phage insensitivity pattern is additive (i.e. in the case of phage which are only partially inhibited by each plasmid on its own, the presence of the two plasmids together gives substantially total insensitivity). In particular, the invention provides lactic streptococcal hosts into which have been introduced plasmids pCI750 and pCI829. The invention also provides isogenic derivatives of these plasmids including Lac-marked derivatives thereof, plasmids which are substantially similar thereto, or plasmids having phage insensitivity encoding DNA which is substantially similar to that of pCI750, pCI829 and pCI528.

The invention especially relates to all of the above-defined materials in biologically pure form or essentially pure form.

The invention further provides dairy starter cultures, particularly cheese starter cultures, containing any of the materials defined above. The invention also has potential for use in cultures used in meat and meat fermentations such as the manufacture of "German" sausage, vegetable fermentation cultures and probiotic cultures.

The invention also provides methods of conferring phage insensitivity on a bacterium comprising introducing into the said bacterium a plasmid or a DNA fragment as defined above, and on a food starter culture comprising bacteria in which a plasmid or DNA fragment as defined above is introduced into the said bacteria.

This application more particularly describes three plasmids which confer valuable phage insensitivity against a variety of phage including virulent prolate-headed phage and offer advantages over other plasmids

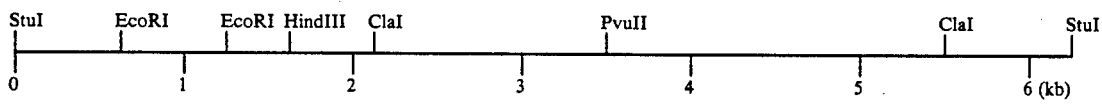

or a fragment spanning two BclI fragments of 13.9 and 1.8 kb derived from pCI750 as deposited in *S. lactis* AB001 at the National Collection of Industrial Bacteria (NCIB), Aberdeen, Scotland, under accession no. 12261 on 16th May 1986, and having the restriction map:

described in the literature. For example, some of the prior art plasmids are non-conjugative and cannot easily be used to construct phage insensitive starter strains. The plasmids pNP40 (1) and pTRT2030 (2-7) are both heat-sensitive in a *S. lactis* background although the

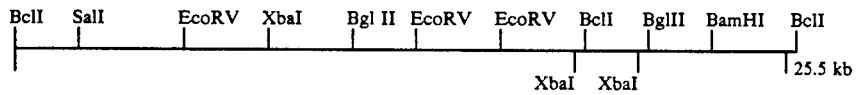

The invention also relates to DNA which is an isogenic derivative of any of the said DNA fragments, latter was heat-insensitive in *S. cremoris* hosts when titred against small isometric-headed phage. In contrast, the plasmids described in this application encode heat insensitive mechanisms effective against prolate-headed phage in both *S. cremoris* and *S. lactis* backgrounds. This is of major importance in commercial cheese-making.

pCI528, based on its ability to inhibit isometric- and prolate-headed phage, is the most potent phage insensitivity plasmid currently available. Furthermore, the additive effect of the mechanisms associated with pCI750 and pCI829 against prolate-headed phage has very significant practical applications.

From a mechanistic viewpoint, pCI750 differs from pTR2030 in that the latter does not inhibit the induction of prophage when present in a lysogenic host whereas pCI750 will cause a very severe reduction in the levels of inducibility. Furthermore, the presence of pTR2030 in a host is unable to reduce the e.o.p. of prolate-headed phage. pCI750 and pCI829 can reduce the e.o.p. by between 0.5 and seven log cycles. pCI528 is different to pNP40 and pTR2030, in that an effect on phage absorption contributes to its overall phage insensitivity mechanism.

The DNA fragment isolated from pCI829 can be used as a probe to identify the plasmid pCI829 as deposited at the NCIB under accession number 12263 and plasmids having phage insensitivity encoding DNA which is substantially similar to that of pCI829, while the DNA fragment isolated from pCI750 can be used as a probe to identify the plasmid pCI750 as deposited at the NCIB under accession number 12261 and plasmids having phage insensitivity encoding DNA which is substantially similar to that of pCI750.

BRIEF DESCRIPTION OF THE DRAWINGS

The present invention will now be described with reference to the accompanying drawings which show the following.

Lane 1—Lambda-EcoRl standard digest.
Lane 2—BclI digested pCI750 generating fragments of 17.1, 13.9, 12.4, 11.3, 5.2, 3.7 and 1.8 kb.
Lane 3—BclI digested pMM1 showing that the 13.9 and 1.8 kb fragments from pCI750 had been cloned in pGB301.
Lane 4—BclI digested pGB301 (i.e. the plasmid is linearized).

Figure 17:
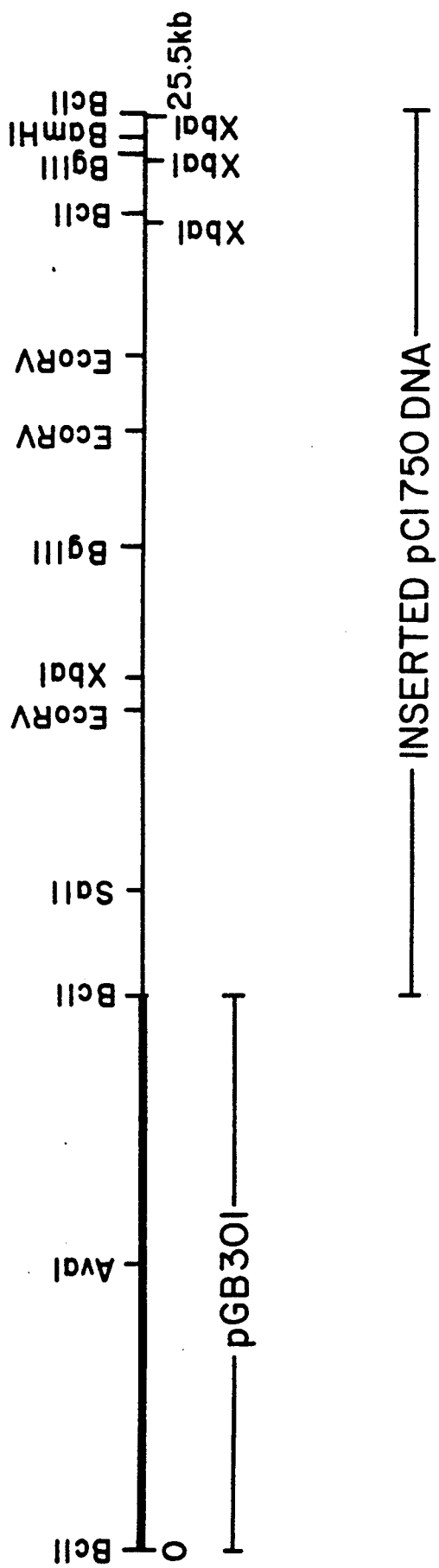

FIG. 17 Detailed restriction map of the cloned DNA from pCI750 containing the 13.9 and 1.8 kb BclI fragments.

Figure 18:
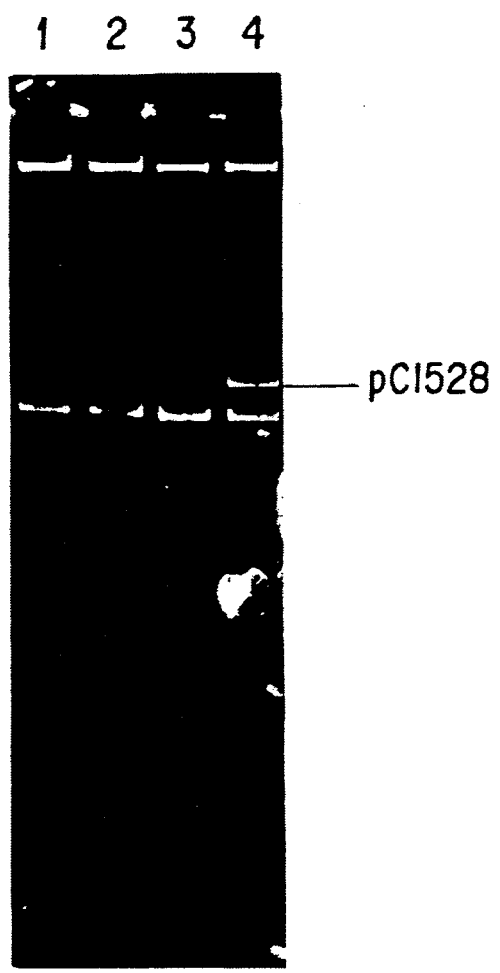

FIG. 18 Agarose gel (0.7%) showing plasmid profiles of S. cremoris UC503 and selected plasmid cured derivatives Lane 1-3—Phage sensitive derivatives of S. cremoris UC503 cured of the 28 Mdal pC1528 plasmid. Strain UC563 is shown in lane 2.
Lane 4—S. cremoris UC503 harbouring plasmids of 46, 33, 28, 17, 4.0 and 2.1 Mdal FIG. 19 Agarose gel (0.7%) showing the construction of a strain of S. lactis harbouring the phage insensitive plasmid pCI528 from S. cremoris UC503.

Lane 1—S. cremoris UC503
Lane 2—S. cremoris UC563 cured of pCI528
Lane 3—S. cremoris UC503 containing pAMBI
Lane 4—S. lactis UC504—i.e. S. lactis transformant containing pCI528, pAMBI and two cryptic plasmids from strain UC503
Lane 5—S. cremoris UC504 cured of pAMBI
Lane 6—S. lactis 505 cured of pLP712
Lane 7—S. lactis 505 containing pLP712 and pCI829
Lane 8—S. lactis MG1299 containing pLP712

Figure 20:
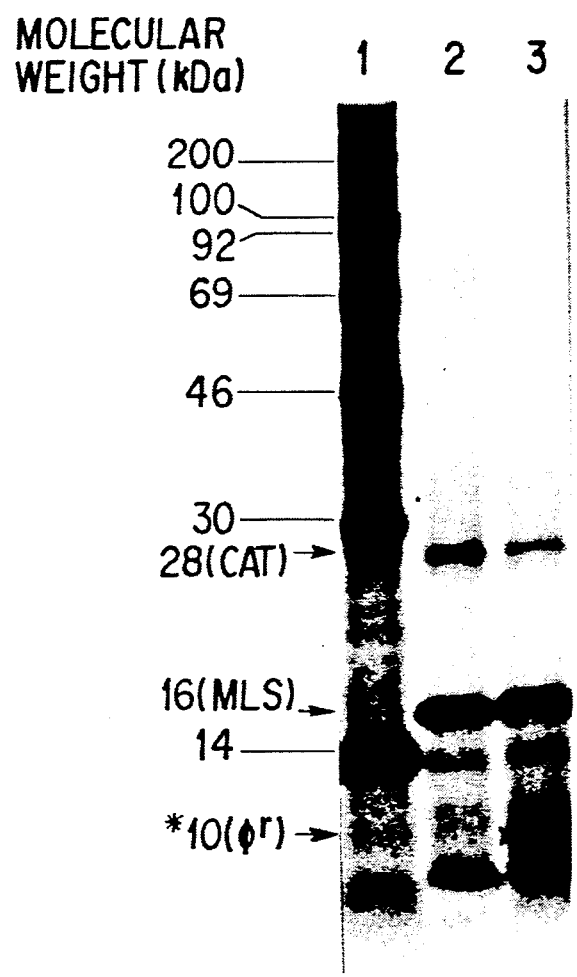

FIG. 20 Autoradiogram showing protein products generated by E. coli maxicells containing either pSA3 or pCI816 following labelling with $^{35}S$ methionine.

Lane 1—Molecular weight standards all labelled with $^{14}C$

|  | mw |
| --- | --- |
| Myosin | 200,000 |
| Phosphorylase B | 100,000 |
| " | 92,500 |
| Bovine serum albumin | 69,000 |
| Ovalbumin | 50,000 |
| " | 46,000 |
| Carbonic anhydrase | 30,000 |
| Lysozyme | 14,000 |

Lane 2—Protein products generated by pSA3. The product of the cat and mls genes are indicated.
Lane 3—Protein products generated by pCI816. The products of the cat and mls genes are indicated as is the novel 10 kDa product generated by the inserted 6.3 kb StuI fragment.

DESCRIPTION OF THE INVENTION

PLASMID

A plasmid is an extrachromosomal DNA molecule capable of autonomous replication.

Plasmids pCI750 is a 43.6 Mdal (66 kb) plasmid originally identified in S. cremoris UC653. This plasmid can be conjugatively transferred to Group N streptococcal recipients where it confers insensitivity to bacteriophage infection. S. lactis AB001 strain containing this plasmid has been deposited at the National Collection of Industrial Bacteria (NCIB), Aberdeen, Scotland under Accession No. 12261 on 16th May 1986.

pCI777 is a 77 Mdal plasmid generated following in vivo cloning of lactose utilization genes in the phage insensitivity plasmid after a conjugation experiment between S. cremoris UC653 and S. lactis MG1363Sm. It encodes phage insensitivity, lactose utilization and high frequency conjugative ability. S. lactis AB002 strain containing this plasmid has been deposited at the NCIB under Accession No. 12262 on 16th May 1986. It is representative of plasmids pCI751 and pCI783.

pCI751 is a 51 Mdal plasmid generated following in vivo cloning of lactose utilization genes in the phage insensitivity plasmid after a conjugation experiment between S. lactis AB001 and S. lactis LM0230Sp. It encodes phage-insensitivity, lactose utilization and high frequency conjugative ability.

pCI783 is an 83 Mdal plasmid generated following in vivo cloning of lactose utilization genes in the phage insensitivity plasmid after a conjugation experiment between S. cremoris UC653 and S. lactis MG1363Sm. It encodes phage insensitivity and lactose utilization.

pCI829 is a 27 Mdal (44 kb) plasmid originally identified in Streptococcus lactis UC811 (formerly BA2). This plasmid can be conjugatively transferred to Group N streptococcal recipients where it confers insensitivity to bacteriophage infection. S. lactis AC001 strain containing this plasmid has been deposited at the NC1B under Accession No. 12263 on 16th May 1986.

pCI528 is a 28 Mdal (43 Kb) plasmid originally identified in S. cremoris UC503. This plasmid can be introduced to group N streptococcal recipients either by transformation or conjugation where it confers insensitivity to bacteriophage infection. S. cremoris UC505 strain containing this plasmid has been deposited at the NCIB under Accession No. 12478 on 18th May 1987.

pAM401—is a vector plasmid which is capable of replicating in E. coli and members of the genus Streotococcus. The plasmid is 10.4 kb in size and encodes chloramphenicol (Cm), and tetracycline (Tc) resistance. This plasmid was obtained from D. Clewell, University of Michigan, Ann Arbor, Mich., U.S.A.

pVA838—is a vector plasmid which is capable of replicating in E. coli and members of the genus Streotococcus. The plasmid is 9.2 kb in size and encodes erythromycin (Em) and chloramphenicol (Cm) resistance. This plasmid was obtained from D. Clewell, University of Michigan, Ann Arbor, Mich., U.S.A.

pCI801—a recombinant plasmid derived following the cloning of a 4.0 kb BqlII fragment from pCI829 into the unique BamHI site of pAM401 and which confers insensitivity to phage 712 when introduced into S. lactis MG1363.

pSA3 is a shuttle vector plasmid capable of replicating in E. coli and streptococci and is 10.2. kb in size. The construction of pSA3 was described by Dao and Ferretti (34) and it was obtained from Prof. L. L. McKay, University of Minnesota, U.S.A.

pGB301 is a streptococcal plasmid vector and is 9.8 kb in size (35). This vector was obtained from Prof. L. L. McKay, University of Minnesota, U.S.A.

pCI816 is a recombinant plasmid constructed by cloning a 6.3 kb StuI fragment from PCI829 into the unique NruI site of pSA3 and which confers reduced sensitivity to phage 712 when introduced into *S. lactis* MG1363.

pMM1 is a recombinant plasmid which contains two BclI fragments of 13.9 and 1.8 kb from PCI750 inserted into pGB301 at its unique BclI site. This plasmid confers reduced sensitivity to phage 712 when introduced into *S. lactis* LM0230.

Group N Streptococci

This group of bacteria includes three species of the genus Streotococcus—*S. lactis, S. cremoris* and *S. lactis* subsp. diacetylactis. These bacteria may also be termed the mesophilic lactic streptococci.

*S. cremoris* UC653

*S. cremoris* UC653 is a strain originally isolated from a mixed strain starter culture. This strain has been used as a component of a defined strain starter used in commercial Cheddar cheese-making and is deposited in the Stock Culture Collection, Dairy and Food Microbiology Department, University College, Cork. It has also been deposited at the NCIB under Accession No. 12265 on 20th May 1986.

*S. cremoris* UC503

*S. cremoris* UC503 is a strain originally isolated from a mixed strain starter culture used in commercial cheddar cheese-making. It was deposited at the NCIB under Accession No. 12477 on 18th May 1987. This strain was previously named *S. cremoris* F.

*S. cremoris* UC563

*S. cremoris* UC563 is a derivative of *S. cremoris* UC503 cured of its 28 Mdal phage insensitivity plasmid following acriflavin (25 μg/mL) treatment. This strain is significantly more sensitive to phage UC503 and is also sensitive to phage c2 and UC811 which are incapable of plaquing on *S. cremoris* UC503.

*S. Lactis* UC811 (formerly BA2)

*S. lactis* UC811 is a classical "laboratory strain" and is deposited in the Stock Culture Collection, Dairy and Food Microbiology Department, University College, Cork. It has also been deposited at the NCIB under Accession No. 12266 on 20th May 1986. This strain was previously named *S. lactis* BA2.

*S. lactis* MG1363 Sm

*S. lactis* MG1363 Sm is a plasmid-free derivative of *S. lactis* 712 obtained from M. Gasson, Food Research Institute, Reading, U.K. and made resistant to Streptomycin in the present inventors' laboratory. This strain was used as a recipient in conjugation experiments.

*S. lactis* MG1229

*S. lactis* MG1229 is a derivative of *S. lactis* 712 cured of all its native plasmids except pLP712, a Lac/Prt plasmid. This strain was obtained from M. Gasson, Food Research Institute, Reading, U.K. and was used as a recipient in conjugation experiments.

*S. lactis* MG3020

*S. lactis* MG3020 is a derivative of *S. lactis* MG1363 Sm containing the broad host range plasmid pAMBI (17 Mdal). In addition to the erythromycin (Em) resistance encoded on pAMBI, this strain is resistant to streptomycin and was obtained from M. Gasson, Food Research Institute, Reading, U.K.. This strain was used as a donor of pAMBI in conjugation experiments.

*S. lactis* LM0230 Sp

*S. lactis* LM0230 Sp is a plasmid-free bacteriophage-sensitive derivative of *S. lactis* C2 obtained from L. L. McKay, University of Minnesota, St. Paul, Minn., USA. This strain was used as a recipient in conjugation experiments.

*S. lactis* LM2305

*S. lactis* LM2305 is a plasmid-free, bacteriophage-sensitive neomycin sulphate resistant isolate of *S. lactis* C2 obtained from L. L. McKay. University of Minnesota, St. Paul, Minn., USA. This strain was used as a recipient in conjugation experiments.

*S. lactis* MMS366

*S. lactis* MMS366 is a Lac$^-$bacteriophage sensitive recombin deficient (Rec$^-$) rifampin resistant isolate of *S. lactis* ML3 containing plasmids of 31.9, 5.6, 1.98 and 1.0 Mdal, obtained from L. L. McKay, University of Minnesota, St. Paul, Minn., USA. This strain was used as a recipient in conjugation experiments.

*S. lactis* LM 3301

*S. lactis* LM 3301 is a Lac$^-$, bacteriophage sensitive, Streptomycin resistant derivative of *S. lactis* ML3 containing plasmids of 31.9, 5.6, 1.98 and 1.0, obtained from L. L. McKay, University of Minnesota, St. Paul, Minn., U.S.A.

*S. lactis* SK3 Lac-Tc$^R$

*S lactis* SK3 Lac-Tc$^R$ is a lactose negative (Lac$^-$) tetracycline resistant (Tc$^R$) derivative of S. Lactis SK3. The strain was made Lac$^-$ following subculture at 37° C. and made Tc$^R$ after the conjugal introduction of the transposon Tn919 in the present inventors' laboratory. *S. lactis* SK3 Lac-Tc$^R$ was used as a recipient in conjugation experiments.

*S. lactis* subsp. diacetylactis 18–16 Lac-Tc$^R$

*S lactis* subsp. diacetylactis 18–16 Lac-Tc$^R$ is a Lac-Tc$^R$ derivative of *S. lactis* subsp. diacetylactis 18–16 constructed in a manner identical to that described above for *S. lactis* SK3 Lac-Tc$^R$. *S. lactis* subsp. diacetylactis 18–16 Lac-Tc$^R$ was used as a recipient in conjugation experiments.

*S. lactis* subsp. diacetylactis 18–16 Lac-S

*S. lactis* subsp. diacetylactis 18–16 Lac-S is a Lac$^-$ streptomycin resistant derivative of *S. lactis* subsp. diacetylactis 18–16 and was used as a recipient in conjugation experiments.

*S. cremoris* UC411 Lac-Fus$^R$

*S. cremoris* UC411 Lac-Fus$^R$ is a Lac$^-$ (made by subculture at 37° C.) fusidic acid resistant (Fus$^R$) derivative of *S. cremoris* UC411. This strain was made resistant to Fus by plating $10^9$ cells on plates containing 25 μg/ml Fus and selecting spontaneous resistant mutants.

Transformant

Transformants are defined as cells arising from the introduction of naked DNA (plasmid DNA in the case of this study) into protoplasted recipients.

*S. lactis* UC504

*S. lactis* UC504 is a transformant arising from the treatment of protoplasts of *S. lactis* MG1363 Sm with total plasmid DNA from S. cremoris UC503 (pAMBI). S. lactis UC504 harbours pCI528 (28 Mdal). pAMB1 (17 Mdal) and two cryptic plasmids of 18.0 and 2.1 Mdal from S cremoris UC503.

Transconjugant

Transconjugants are defined as cells arising from the conjugative transfer of DNA from a donor to a recipient bacterium.

S. lactis AB001

This is a transconjugant arising from a conjugation experiment between the S. cremoris UC653 donor and the S. lactis MG1363 Sm recipient. S. lactis AB001 harbours plasmids of 26 Mdal (pCI726, encodes ability to utilize lactose) and 43.6 Mdal (pCI750, encodes bacteriophage insensitivity). It has been deposited at the NCIB under Accession No. 12261 on 16th May 1986.

S. lactis AB002

This is a transconjugant arising from a conjugation experiment between the S. cremoris UC653 donor and the S. lactis MG1363 Sm recipient. S. lactis AB002 harbours a single plasmid of 77 Mdal (pCI777, encodes both lactose utilization and bacteriophage insensitivity). This strain exhibits a high frequency conjugative capacity. It has been deposited at the NCIB under Accession No. 122612 on 16th May 1986.

S. lactis AB003

This is a transconjugant arising from a conjugation experiment between the S. cremoris UC653 donor and the S. lactis MC1363 Sm recipient. S. lactis AB003 harbours a single plasmid of 83 Mdal (pCI783, encodes both lactose utilization and bacteriophage insensitivity).

S. lactis AC001

This is a transconjugant arising from a conjugation experiment between the S. lactis UC811 donor and the S. lactis MG 1363 Sm recipient, harbouring plasmids of 27 Mdal (pCI829, encodes bacteriophage insensitivity) and 42 Mdal (pCI842, encodes lactose utilization). It has been deposited at the NCIB under Accession No. 12263 on 16th May 1986.

S. lactis AC003

This is a transconjugant arising from a conjugation experiment between the S. lactis AB012 donor and the S. lactis AC001 Lac− recipient. S. lactis AC003 harbours plasmids of 51 Mdal (pCI751. encodes both lactose utilization and bacteriophage insensitivity) and 27 Mdal (pCI829, encodes bacteriophage insensitivity).

S. lactis MM20

S. lactis MM20 is a transconjugant arising from a conjugation experiment between the S. cremoris UC653 donor and S. lactis MMS366 recipient harbouring plasmids of 26 Mdal (pCI726, encodes lactose utilization genes) and 43.6 Mdal (pCI750, encodes bacteriophage insensitivity).

S. lactis MM21

S. lactis MM21 is a transconjugant arising from a conjugation experiment between the S. cremoris UC653 donor and the S. lactis MMS366 recipient harbouring a single plasmid of 60 Mdal (pCI760, encodes both lactose utilization and bacteriophage insensitivity).

S. lactis UC505

S. lactis UC505 is a transconjugant arising from a conjugation experiment between S. lactis UC504 donor and the S. lactis MG1299 recipient. This transconjugant harbours pCI528 (28 Mdal) and pLP712 (33 Mdal). It has been deposited at the NCIB under Accession No. 12478 on 18th May 1987.

E. coli LE392 (pAM401)

This strain was used as source of the pAM401 cloning vector. This plasmid, originally obtained from D. Clewell, University of Michigan, Ann Arbor, Mich., USA, was introduced into E. coli LE392 in the present inventors' laboratory.

Bacteriophage (phage)

Bacteriophage are viruses capable of infecting bacteria.

Phage 712, SK1, StL5, Eb1 and c2 are capable of infecting (i.e. lytic for) S. lactis MG1363 Sm. The phage c2 is a prolate-headed phage (29), while the phage 712 is generally accepted in the field to be a small isometric-headed phage and was shown to be so by morphological examination in the present inventors' laboratory.

Phages 18-16 and drc3 are capable of infecting S. lactis subsp. diacetylactis 18-16S.

Phage uc503 infects S. cremoris UC503 while phages uc503, c2 and uc811 infect mutants cured of the 28 Mdal plasmid. Phages sk3 and uc411 are capable of infecting hosts S. lactis SK3 Lac-Tc$^R$ and S. cremoris UC411 Lac-Fus$^R$ respectively.

Bacterial strains, bacteriophage and media

Other bacterial strains

E. coli CSR603 was obtained from the stock culture collection, Microbiology Department, University College, Cork where it is publicly available. This strain is sensitive to ultra-violet light and was used in the maxicell in vivo transcription-translation studies to analyse the product(s) of the 6 kb StuI fragment from pCI829.

The bacterial strains were routinely grown in the M17 medium of Terzaghi and Sandine (8) in which glucose replaced lactose when required (GM17). Solid media contained 1.5% agar (Oxoid No. 3). The antibiotics (Sigma, U.K.) streptomycin (Sm) and spectinomycin (Sp) were added to selective media at levels of 600 μg/ml and 150 μg/ml, respectively. The method used to generate spontaneous antibiotic resistance mutants of lactic streptococci has been previously reported by Hill et al. (9).

Conjugation experiments

Agar surface matings were carried out as described by McKay et al. (10). Lactose indicator (LIA) of McKay et al. (11) containing the appropriate antibiotic was used to select for Lac transfer. Sensitivity of Lac, transconjugants to phage was determined using the spot test method. Briefly, this involved incorporating 0.1 ml of the fully grown test cultures into an M17 soft agar (0.7%) overlay which was poured on a hard M17 agar (1.5%) plate. After solidifying 10 μl aliquots of the appropriate phage suspension ($10^8$ pfu/ml) were spotted onto the overlay. Results were read after overnight incubation at 30° C.

Frequency of transfer

The frequency of transfer of a specific marker (i.e. Lactose utilization or phage insensitivity) refers to the number of transconjugants obtained divided by the number of recipients and is described as the frequency per recipient.

Transformation of E. coli

E. coli LE392 were transformed by the Calcium chloride-heat shock method of Mandel and Higa (31).

Assay of phage sensitivity

Sensitivity of specific strains to bacteriophage was determined using a "spot test" as described above in Conjugation Experiments.

Determination of effect of temperature on phage insensitivity mechanism.

The effect of elevated temperature (up to 40° C.) on the phage insensitivity mechanisms was determined by assaying phage (preheated to the appropriate temperature) on the culture (preheated) and then incubating the assays at the desired temperature.

Milk activity tests

The activity test described by Heap and Lawrence (4) was used to determine the effectiveness of the phage insensitivity mechanisms in simulated laboratory cheese-making trials.

Bacteriophage adsorption 0.6 ml of the phage suspension ($10^5$ pfu/ml) was added to a 1.5 ml microcentrifuge tube containing 0.2 ml $CaCl_2$ (0.185 M) and 0.6 ml of the fully grown test culture resuspended in M17 (pH 7.5). The tube was mixed vigorously for 10 sec and then incubated at 30° C. for 12 min to allow adsorption to occur. After cooling on ice to stop the reaction, the tubes were centrifuged in a microfuge (Eppendorf) for 10 min to pellet the cells and adsorbed phage. A 1.0 ml sample of the supernatant was removed and titred for phage using a sensitive host as indicator. Percent phage adsorbed was determined as [(control titre—residual titre)/control titre]×100.

Isolation and analysis of plasmid DNA

The method of Anderson and McKay (14) was used to isolate plasmid DNA from streptococci and E. coli V517. Plasmid profiles were analysed by electrophoresis on 0.7% agarose (Sigma, U.K.) gels using a vertical gel apparatus. Electrophoresis was carried out in TAE buffer (40 mM Tris, 10 mM $Na_2EDTA$, 12 mM sodium acetate. pH 7.8). Gels were stained in ethidium bromide solution (5 μg/ml) and DNA was visualised with short-wave UV light.

Restriction mapping, hybridization analysis and molecular cloning

Digestions with restriction endonucleases were carried out as described by Maniatis et al. (15). Restriction maps of pCI750. pCI829 and pCI528 were prepared as described by Coveney et al. (16). The restriction map of pCI829 was constructed by the comparison of single, double and triple restriction digests of the plasmid. For pCI750 the location of the cleavage sites of three restriction endonucleases has been accurately determined (FIG. 5) and pCI528 has been mapped for six restriction enzymes (FIG. 6).

Figure 11:
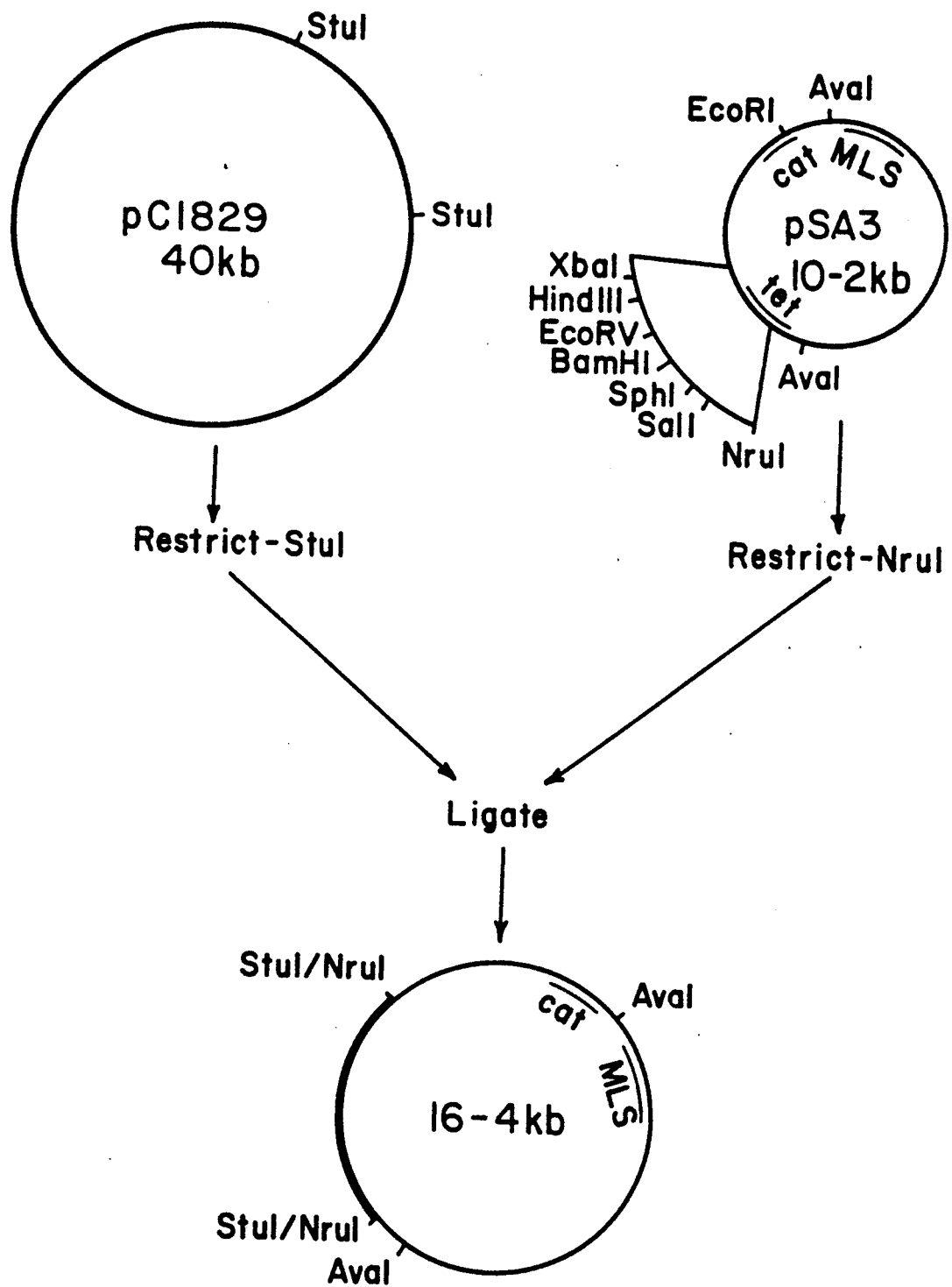
FIG. 11 Outline of strategy used to clone the 6.3 kb StuI fragment harbouring determinant(s) associated with phage insensitivity from pCI829 into the unique NruI site of pSA3.

The Southern blot and hybridization techniques have been described by Southern (17) and Coveney et al. (16). The cloning of specific fragments of pCI829 and pCI750 was performed exactly as described in Maniatis et al. (15) using the restriction endonucleases and the T4 ligase exactly as described by the suppliers. The actual cloning strategy for fragments from pCI829 is outlined in FIG. 11. The phage insensitivity determinant(s) of pCI829 was cloned in E. coli HB101 first and the recombinant plasmid then introduced into S. lactis MG1363 while the phage insensitivity determinant(s) from pCI750 was cloned directly into S. lactis LM0230. Clones containing recombinant plasmids were identified by random screening of the plasmid contents of transformants.

Transformation of E. coli and S. lactis strains

All E. coli strains used in the study were transformed by the calcium chloride-heat shock method of Mandel and Higa (31). Protoplasts of S. lactis MG1363 Sm were made, transformed and regenerated as described by Gasson and Anderson (12). The transforming DNA was total plasmid DNA from S. cremoris UC503 (pAMBI) and transformants were selected on the basis of Em resistance. S. lactis LM0230 was transformed by the method of Kondo and McKay (32). Transformation of S. lactis MG1363 was achieved by electroporation as follows:

1. An active culture was inoculated (1%) into GM17 medium (8) supplemented with 40 mM d-1-threonine and grown to an O.D. (660 nm) of 0.2.
2. The cells were harvested, washed twice in 5 ml electroporation buffer (EB; 5 mM potassium phosphate pH 7.4, 0.3 M sucrose and 1 mM magnesium chloride), resuspended in EB and kept on ice for 10 min.
3. The cell suspension (0.8 ml) was mixed with 1–5 μg of transforming DNA (amount varied with the particular experiment) in a cuvette and electroporation was performed at 2000 volts at 25 μF.
4. Following electroporation, the cells were held on ice for 10 min, were diluted 10-fold in SGM17 (i.e. GM17 broth containing 0.5 M sucrose) and incubated at 30° C. for 2 h before spread plating 0.1 ml aliquots on SGM17 agar containing the appropriate antibiotics.
5. Plates were incubated at 30° C. for 2 days and the number of transformants determined.

Identification of protein products encoded by the cloned 6.3 kb StuI fragment from pCI829

The product(s) of the 6.3 kb StuI fragment cloned from pCI829 were analysed using the maxicell system exactly as described by Sancar et al. (33). pSA3 and pCI816 were introduced into E. coli CSR603 by transformation and following irradiation with UV light the cells were labelled with $^{35}S$ methionine. After washing, the cells were lysed by boiling, run on a polyacrylamide gel which was then exposed to X-ray film after drying.

Results

Conjugative transfer of lactose utilization and phage insensitivity from S. cremoris UC653 and S. lactis UC811

Markers associated with lactose utilization and phage insensitivity were transferred from S. cremoris UC653 and S. lactis UC811 donors to a S. lactis MG1363 Sm recipient in agar surface matings (10). The transfer frequencies are shown in Table 1.

Transconjugants from these matings were designated AB001, AB002 and AB003 or AC001 depending on whether they are derived from the strain UC653 or UC811 donors, respectively. All these transconjugants were totally insensitive to phage 712 and allowed phage c2 to plaque with a reduced size. Both phage are lytic for strain MG1363.

Figure 1:
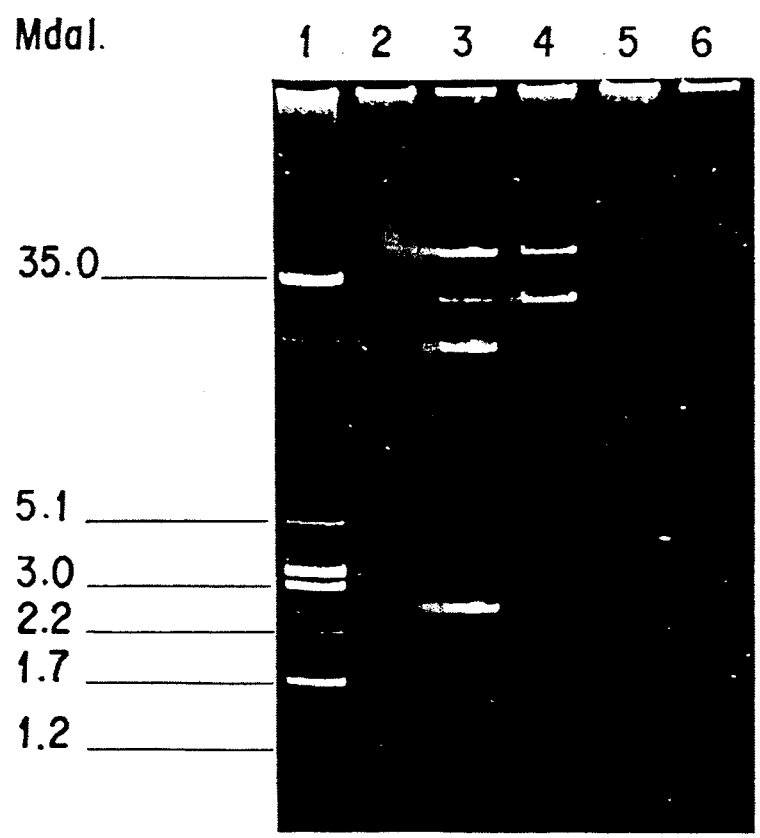
FIG. 1 Agarose gel (0.7%) showing plasmids from *S. cremoris* UC653 and selected Lac+ phage insensitive transconjugants.
  Lane 1—*E. coli* V517 molecular weight standards
  Lane 2—Plasmid-free *S. lactis* MG1363 Sm recipient
  Lane 3—*S. cremoris* UC653 donor containing 6 plasmids of 44, 26, 15, 10, 2.6 and 1.6 Mdal.
  Lane 4—*S. lactis* AB001 containing 43.6 Mdal pCI750 and 26 Mdal pCI726
  Lane 5—*S. lactis* AB003 containing 83 Mdal plasmid
  Lane 6—*S. Lactis* AB002 containing 77 Mdal plasmid FIG. 2 Agarose gel (0.7%) showing plasmid profiles of *S. Lactis* UC811 and selected Lac+ phage insensitive transconjugants
  Lane 1—*E. coli* V517 molecular weight standards
  Lane 2—Plasmid-free *S. lactis* MG1363 Sm recipient
  Lane 3—*S. lactis* UC811 donor containing plasmids of 42, 27, 24.5, 15, 12.5, 6.5, 5.0, 3.6, 2.0, 1.5, 1.4 Mdal
  Lane 4—Transconjugants AC001 harbouring 27 Mdal pCI829 and 42 Mdal pCI842
  Lane 5–7—Selected transconjugants harbouring different plasmids from strain UC811
Figure 2:
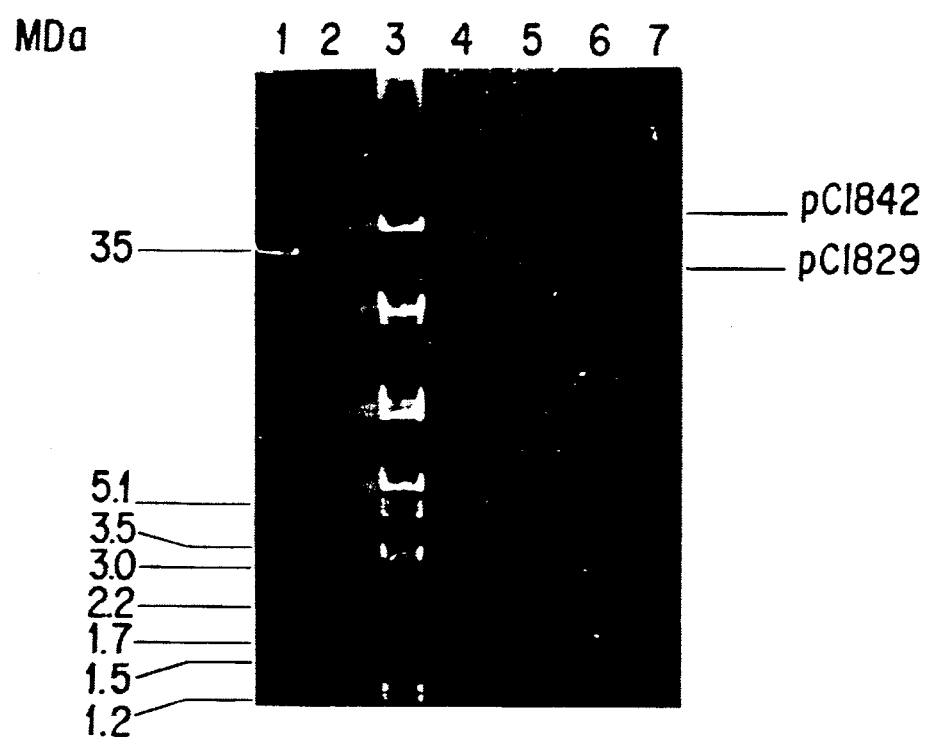

Plasmid profile analysis of transconjugants derived from S. cremoris UC653 and S. lactis UC811 donors The three Lac+ phage 712 insensitive transconjugants isolated from the UC653×MG1363 mating were lysed by the method of Anderson and McKay (14) and their plasmid profiles were analysed. S. lactis AB001 contained two plasmids of 43.6 Mdal (pCI750) and 26 Mdal (pCI726) while S. lactis AB002 and S. lactis AB003 each harboured single plasmids of 77 Mdal (pCI777) and 83 Mdal (pCI783), respectively (FIG. 1). The S. lactis AC001 transconjugant (also Lac, phage 712 insensitive) contained two plasmids of 27 Mdal (pCI829) and 42 Mdal (pCI842) (FIG. 2).

Further mating experiments between the AB001 and AC001 donors and a S. lactis LM0230 Sp recipient were completed (Table 1). Transconjugants showed the same resistance patterns as did AB001 and AC001—i.e. partial insensitivity to phage c2 and total insensitivity to phage 712. A phenotypically representative transconjugant derived from the AB001×LM0230 mating was designated S. lactis AB012 and this harboured a recombinant Lac/phage insensitivity plasmid of 51 Mdal (pCI751).

Analysis of the conjugative abilities of lactose utilization and phage insensitivity plasmids Further mating experiments comparing the ability of AB001 and AB002 to act as donors showed that AB002 could transfer Lac (and phage insensitivity) at frequencies approximately four log cycles higher than AB001 (Table 2). This indicated that pCI777 which is present in S. lactis AB002 harbours genes conferring an ability to transfer at high frequency.

The pCI750 plasmid present in S. lactis AB001 was removed using plasmid curing treatments. Isolates missing this molecule reverted to phage 712 sensitivity. However, these isolates still harboured pCI726 and remained Lac+ confirming that pCI726 encoded lactose utilization genes while pCI750 encoded phage 712 insensitivity. Furthermore, repeated attempts to transfer pCI726 to S. lactis LM2306 in conjugation experiments were unsuccessful indicating that pCI750 harboured genes conferring conjugative ability in addition to phage insensitivity.

A conjugation experiment between the S. cremoris UC653 donor and the S. lactis MMS336 recipient (which is recombination-deficient) also yielded Lac+, phage 712 insensitive transconjugants (Table 2). However, these were of two types, (a) S. lactis MM20 contained two plasmids of 43.6 Mdal (i.e. pCI750) and 26 Mdal (i.e. pCI726) and (b) S. lactis MM21 contained a single plasmid of 60 Mdal. This latter result shows that recombination between pCI750 and pCI726 (or parts thereof) can still occur in a Rec− strain suggesting that recombination is Rec independent.

Figure 3:
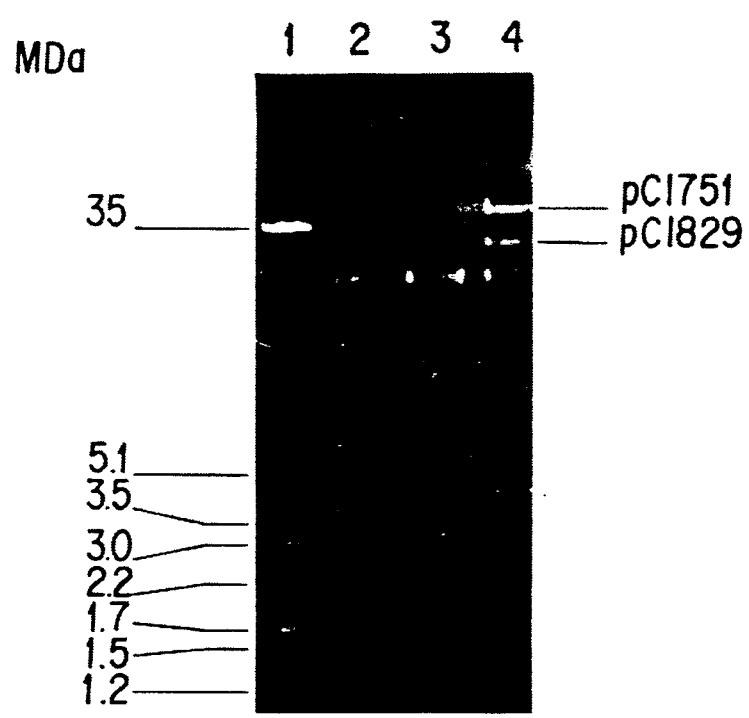
FIG. 3 Construction of an *S. lactis* strain harbouring two phage insensitive plasmids—pCI829 and pCI751.
  Lane 1—*E. coli* V517 molecular weight standards
  Lane 2—Lac− AC001 harbouring pCI829 alone and used as a recipient
  Lane 3—Donor strain AB012 harbouring pCI751
  Lane 4—*S. lactis* AC003 containing pCI751 and pCI829

Introduction of the phage insensitivity mechanism encoded on pCI750 to a strain harbouring pCI829 i.e. construction of a strain containing two phage insensitivity plasmids The phage insensitivity genes encoded on pCI750 were introduced on pCI751 (derived from pCI750 and containing lac genes) into a Lacderivative of S. lactis AC001 (which still contains pCI829) in conjugation experiments generating transconjugant AC003 (FIG. 3). The effect of the presence of both mechanisms in a single strain was to confer total insensitivity to phage c2 (which was capable of forming plaques on strains harbouring either pCI750 or pCI829 alone) in addition to continuing insensitivity to phage 712. This effect is shown in Table 9 where isolates harbouring pCI750 or pCI829 alone allowed phage c2 to form plaques of 1.5 mm diameter (which are significantly smaller than those formed on strain MG1363 Sm which is plasmid-free). However, all plaquing ability is eliminated in the case of transconjugant AC003 which contains the phage insensitivity mechanisms encoded on both plasmids.

Extent and effectiveness of phage insensitivity conferred by pCI750 and pCI829

The effect of the phage insensitivity plasmids pC1750 and pCI829 on an extended range of phage was examined (Table 3). Plasmid pCI750. present in S. lactis AB001 was capable of conferring total insensitivity to phage skI in a manner identical to the insensitivity conferred against phage 712. Also, the plaque sizes developed by all phage that were capable of plaquing on any of the hosts containing pCI750. pCI829 or the mechanisms encoded by both pCI750 and pCI829 together, were very significantly reduced in size compared to those formed on S. lactis MG1363 Sm (which contains no plasmids). In all cases the reduction in plaque size was greater than 50%. Furthermore, the titre of all the phage virulent for hosts AB001, AC001 and AC003 (with the sole exception of phage m13 plagued on AC001) were all reduced by between 0.5 and 7 log cycles compared with those on S. lactis MG1363 Sm, suggesting that a second mechanism of insensitivity was encoded on these plasmids (i.e. in addition to the mechanism resulting in elimination or reduction of plaque size, Table 3). The manufacturing process in Cheddar cheese-making involves a cooking step where the temperature is increased from 30° C. to 37° C. or greater. The data in Table 3 indicates that temperatures of 37° C. or 40° C. have no adverse effect on the ability of either pCI750 or pCI829 to inhibit phage replication. This means that both plasmids will be suitable for inclusion in strains used in commercial Cheddar cheese-making.

Morphological examination of some of the phage described in Table 3 showed that 712 is a member of the commonly occurring small isometric-headed phage group. However, phages c2 and m13 both have prolate heads (29) and thus are members of the extremely virulent prolate-headed grouping. This may explain why these phage can overcome the protective effect of a single phage insensitivity plasmid. Nevertheless, it is significant that the presence of two plasmids can confer the high degree of insensitivity observed in this study.

Transfer of the phage insensitivity plasmids to selected strains of S. lactis, S. cremoris and S. lactis subsp. diacetylactis The transconjugants AB002 (containing the Lac/-phage insensitivity recombinant plasmid pCI777) and AC003 (containing the phage insensitivity plasmid pCI829 and the recombinant Lac/phage insensitivity plasmid pCI751) were used as donors in a series of conjugation experiments with selected recipients (Table 4). In all cases the recipients were Lac− (isolated following curing treatments at 37° C.) and contained either the tetracycline resistance transposon Tn919 (in the case of strains SK3 and 18–16 ) or were spontaneous fusidic acid (Fus) resistant mutants (in the case of strain UC411) to facilitate selection of transconjugants. In all cases, transfer of the Lac marker was detected at a reasonably high frequency and a high proportion of these Lac, transconjugants were also insensitive to the homologous phage of the original recipient strain (Table 4). These data demonstrate that the phage insensitivity trait can be transferred by conjugation to a range of recipient types.

Milk activity tests

The lactose utilization genes of pCI726 and the phage insensitivity mechanism of pCI750 were introduced into S. lactis subsp. diacetylactis 18–16 S in conjugation experiments from the S. cremoris UC653 donor (frequency of Lac transfer=1.6×10−6 per recipient of which 23% were totally insensitive to phages 18–16 and drc3 which are highly for the 18–16 wild-type strain). Selected phage insensitive 18–16 transconjugants were subjected to milk activity tests to determine the efficiency of the phage insensitivity mechanism in this strain when the culture was subjected to repeated growth cycles in milk at 30° C. and 37° C. in the presence of both phage. Under these simulated cheese-making conditions, the presence of phage 18–16 and drc3 had no effect on the ability of the phage insensitive 18–16 transconjugants to produce normal levels of acid. This result indicated that the phage insensitivity mechanism of pCI750 will have a practical application in commercial practice.

Nature of the phage insensitivity mechanism associated with pCI750 and pCI829

Adsorption tests have shown that the presence of either pCI750 or pCI829 in an S. lactis MG1363 Sm host has no effect on the ability of the phage to adsorb. Furthermore, preliminary studies have been undertaken in the case of pCI750 to demonstrate its effect on the inducibility of prophage. The introduction of pCI750 into a lysogenic host reduced the inducibility of prophage compared to a control not containing the phage-insensitivity plasmid, suggesting that the associated mechanism interferes with DNA replication, protein synthesis or even a later stage in the infectious cycle. This contrasts with the reported effect of pTR2030 from Klaenhammer's laboratory, where it did not interfere with the inducibility of prophage and an effect at the level of the cell surface, cell membrane or some early stage in the lytic cycle was proposed as the mode of action of the plasmid (6).

Restriction mapping of the phage insensitivity plasmids pCI750 and pCI829

An analysis of plasmids pCI750 and pCI829 was carried out using a variety of restriction enzymes. The restriction data is as follows:

| Restriction Enzyme | Number of Fragments | Fragment Size (kb) |
|---|---|---|
| RESTRICTION ANALYSIS OF pCI750 | | |
| BamHI | 2 | 35.6, 30.4 |
| BclI | 7 | 21.32, 13.77, 12.55, 9.75, 4.78, 2.13, 1.69 |
| BglII | Many | Not determined |
| BstEII | 2 | 56.74, 9.26 |
| EcoRV | 6 | 41.69, 11.1, 5.48, 5.26, 1.45, 1.08 |
| HindIII | 11 | 23.22, 12.18, 6.70, 5.08, 4.13, 3.51, 3.28, 2.43, 2.03, 1.85, 1.60 |
| HpaII | 10 | 20.97, 14.51, 10.26, 5.91, 3.35, 3.10, 2.25, 2.19, 1.70, 1.55 |
| PvuII | 5 | 26.01, 20.44, 9.66, 6.54, 8.35 |
| SalI | 4 | 25.33, 20.06, 13.16, 7.51 |
| RESTRICTION ANALYSIS OF pCI829 | | |
| Sac | 1 | 40.0 |
| StuI | 2 | 32.9, 6.9 |
| BglII | 3 | 20.8, 14.4, 4.0 |
| PvuII | 3 | 22.9, 8.3, 5.1 |
| ClaI | 4 | 21.2, 7.4, 6.1, 4.8 |
| EcoRV | 6 | 25.1, 5.9. 4.5, 3.1, 2.7, 2.1 |
| HaeIII | 4 | 25.1, 5.49, 5.0, 4.36 |
| HincII | 6 | 11.8, 5.6, 4.5, 3.8, 2.5, 1.7 |
| AvaI | 5 | 16.3, 12.5, 9.1, 4.6, 3.2 |
| HpaII | 8 | 12.6, 11.9, 10.8, 3.9, 2.4, 2.2, 1.2, 0.4 |
| EcoRI | 8 | 21.0, 12.1. 2.5, 2.1, 1.7, 0.84, 0.69. 0.41 |

It will be noted that there may be small fragments of DNA which were undetected on the gels.

Figure 4:
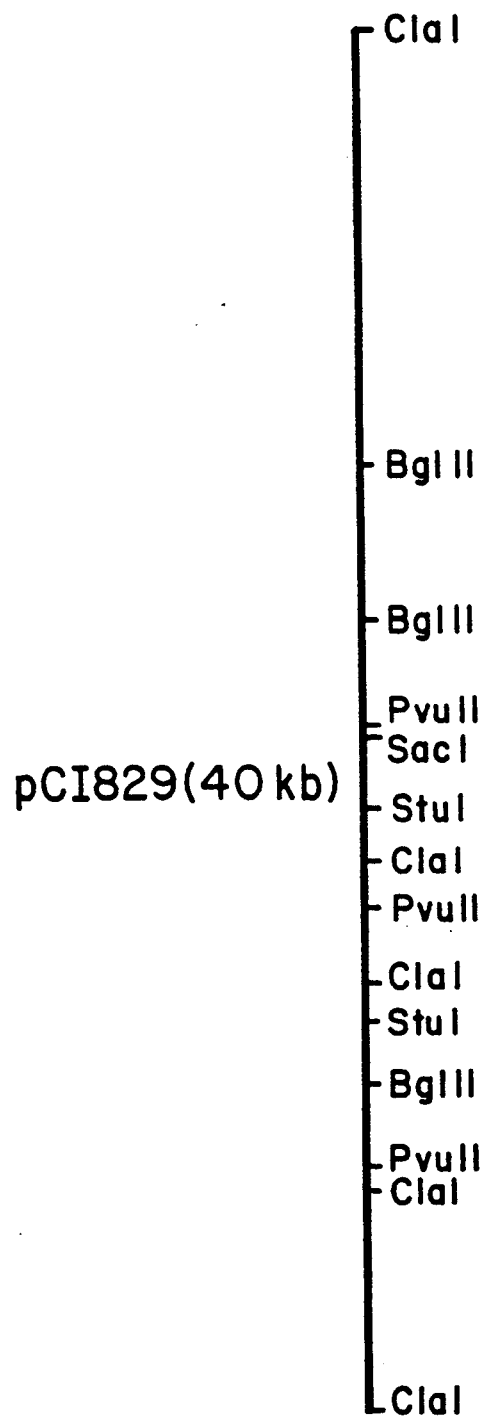
FIG. 4 Restriction map of the phage insensitivity plasmid pCI829.
Figure 5:
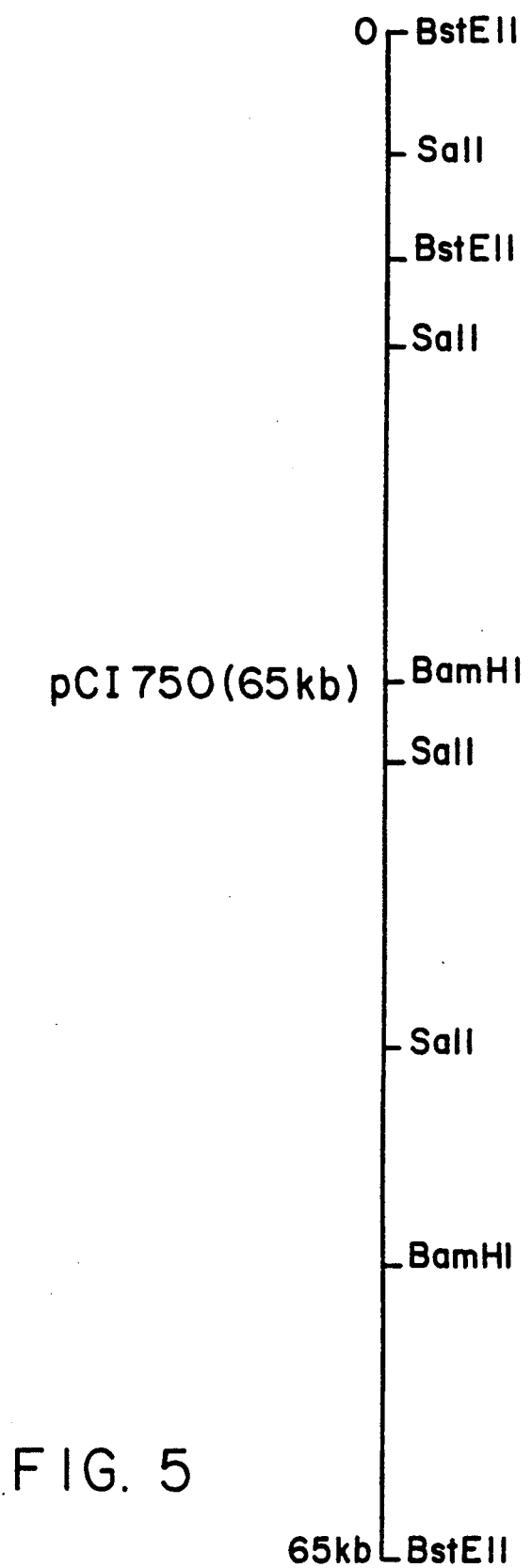
FIG. 5 Restriction map of the phage insensitivity plasmid pCI750.
Figure 6:
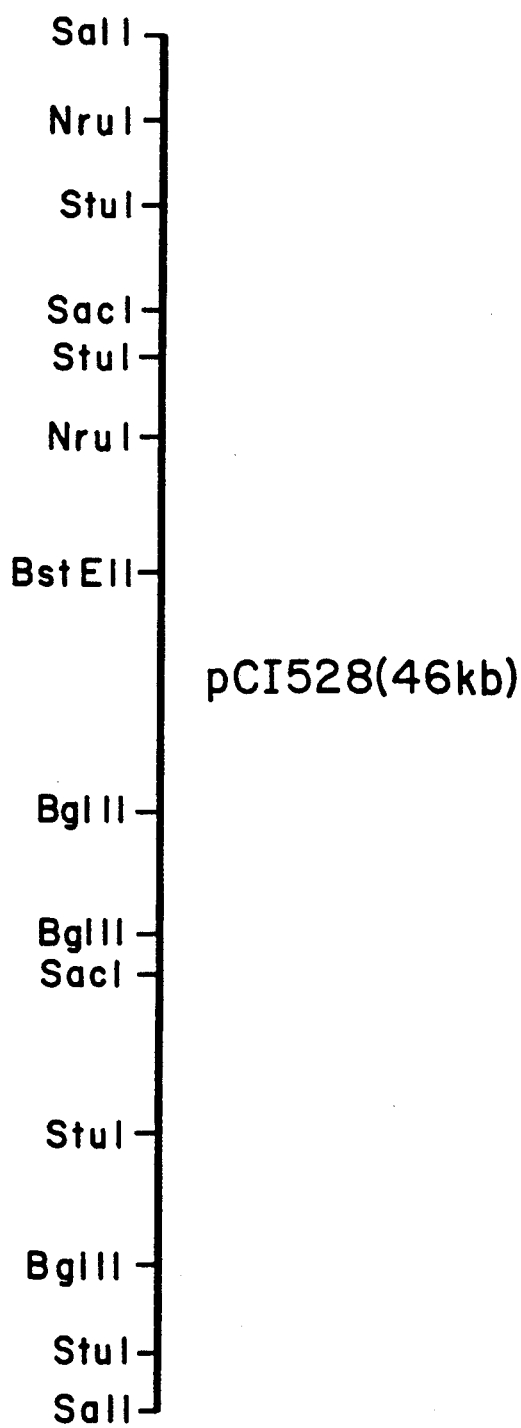
FIG. 6 Restriction map of the phage insensitivity plasmid pCI528.

Restriction maps of pCI829, pCI750 and pCI528 (FIGS. 4–6, respectively, were constructed. The pattern and sequence of the cleavage sites in the maps is typical of the particular plasmid and can be used very easily to identify the different molecules. A Southern blot and hybridization experiment, using pCI750 as a biotin-labelled probe showed no detectable homology between it and pCI829 suggesting that the two plasmids do not share any significant common sequences.

Cloning of the phage insensitivity determinants from pCI829 and pCI750

Figure 7:
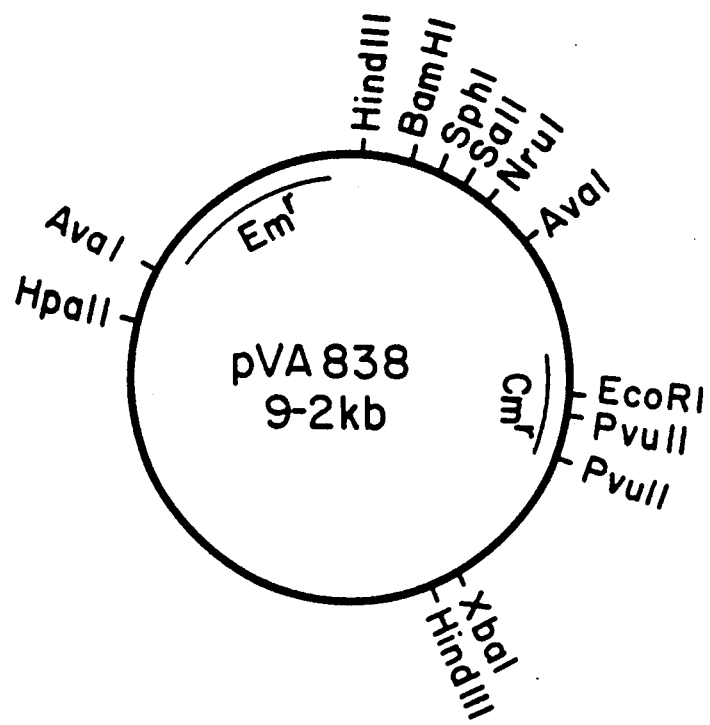
FIG. 7 Plasmid shuttle vector pVA838 used for cloning fragments of pCI829 (from Macrina et al.—see Ref. 30).
Figure 8:
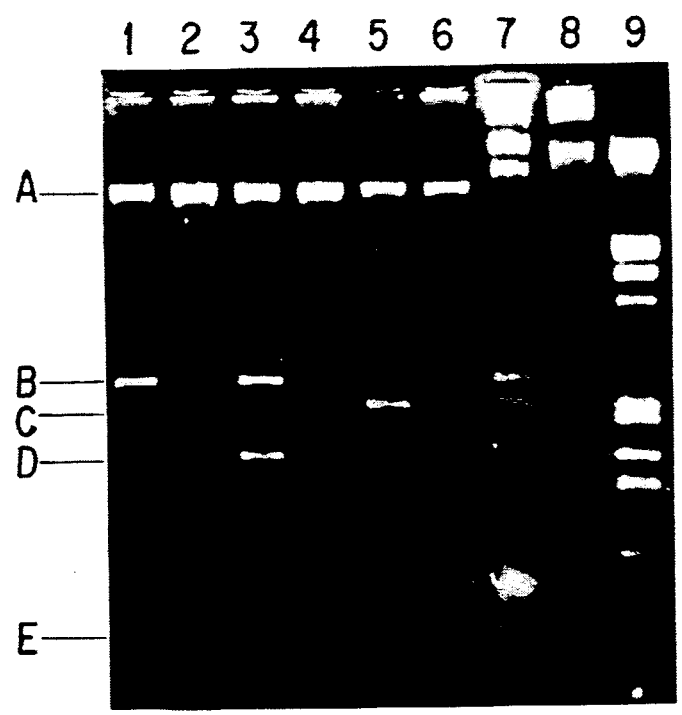
FIG. 8 Agarose gel showing EcoR1 digested pCI829 and recombinant plasmids following cloning in pVA838:
  Lane 1 & 3–5 —EcoR1 digested recombinant plasmids showing linearised pVA838 (9.2 kb) and fragments from pCI129 of 2.5, 21, 1.7 and 0.7 kb
  Lane 7—EcoR1 digest of pCI829 showing fragments of 21, 12, 2.5, 2.1, 1.7, 0.8, 0.7 and 0.4 kb
  Lane 8—Undigested pCI829
  Lane 9—Lambda EcoR1/HindIII Standard digest FIG. 9 Plasmid shuttle vector pAM401 used for cloning fragments of pCI829. (from Wirth et al.—see ref. 18)

There are 8 IcoR1 recognition sites on pCI829. Using a shotgun cloning technique, it was attempted to clone the fragments in E. coli using the E. coli/streptococcus shuttle vector, pVA838 (FIG. 7 (30) which contains a unique EcoR1 site in its CAT gene. Following restriction and ligation, the mix was transformed into E. coli DBII and 5% of the transformants were sensitive to Cm. This insertional inactivation was due to the incorporation of 2.45, 2.14, 1.69 and 0.69 kb fragments from pCI829 into pVA838 (FIG. 8). Attempts to insert the 12.5 and 20 kb fragments were unsuccessful. Each of the four clones was transformed into S. lactic MG1363 but none of the transformants was insensitive to phage 712, indicating that the phage insensitivity gene(s) of pCI829 does(do) not reside on any of the EcoR1 fragments that were cloned.

Figure 9:
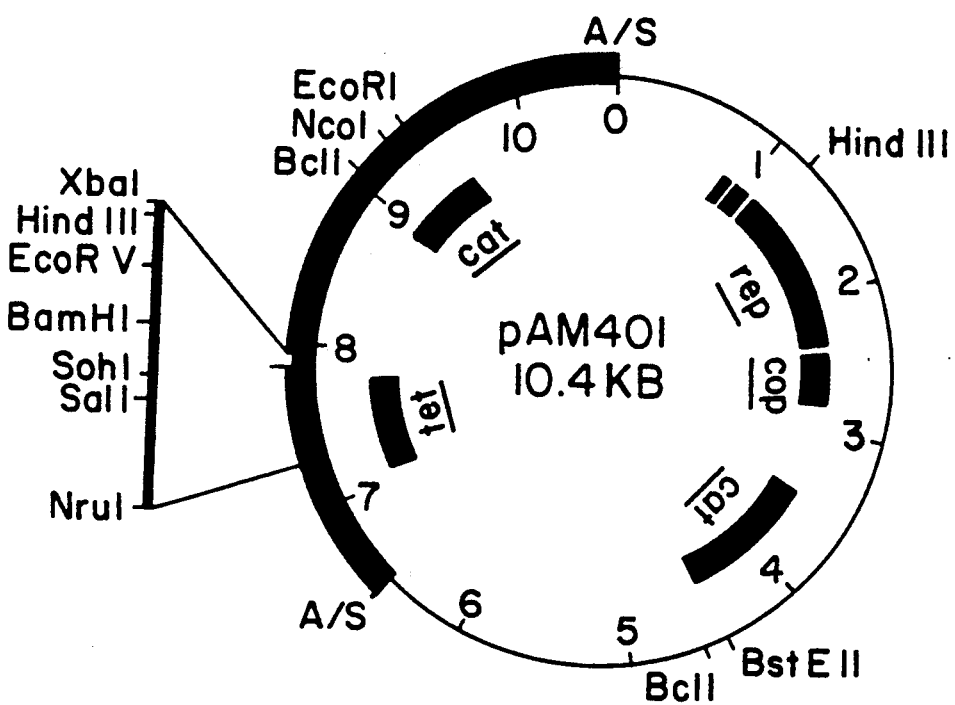
Figure 10:
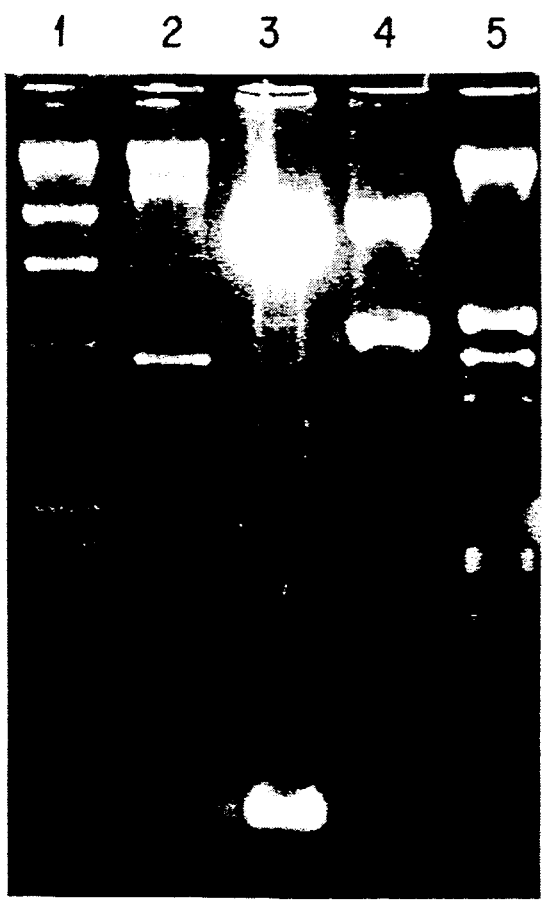
FIG. 10 An agarose gel of the restriction analysis pattern of the recombinant plasmid pCI801, which confers phage insensitivity on *S. lactis* MG1363 (against phage 712):
  Lane 1 & 5—Lambda-EcoR1 and EcoR1/HindIII standard digests, respectively
  Lane 2—pCI829 digested with BqlII generating fragments of 22, 14 and 4kb.
  Lane 3—pAM401 digested with SalI/XbaI generating fragments of 10 and 0.4 kb.
  Lane 4—pCI801 digested with SalI/XbaI generating fragments of 10 and 4.4 kb. The 4.4 kb product consists of the 4.0 kb BqlII fragment of pCI829 and the 0.4 kb SalI/XbaI fragment of pAM401.

Restriction analysis of pCI829 showed that BqlII generated three fragments of 22, 14 and 4 kb. Each of these fragments was isolated from an agarose gel using Whatman DE81 paper and purified. Each fragment was then individually mixed with BamHI linearized pAM401 (FIG. 9 (18) ) and the ligase reaction was allowed to proceed. As expected considering their size, it was not possible to clone the 22 and 14 kb fragments. However, when the 4 kb fragment was used in the cloning experiment, 80% of the chloramphenicol resistant E. coli LE392 transformants were sensitive to tetracycline which is insertionally inactivated at the BamHI site of pAM401. Examination of the clones containing the recombinant plasmid confirmed the presence of a 4 kb insert (FIG. 4) observed as a 4.4 kb SalI/Xba fragment (i.e. the 4 kb insert and 0.4 kb of pAM401 DNA). (FIG. 10). This recombinant plasmid was designated pCI801.

pCI801 was transformed into S. lactis MG1363 protoplasts and Cm resistant transformants (frequency approximately $10^2/\mu g$ DNA) were tested for resistance to phage 712 using the spot test technique. A transformant harbouring the recombinant plasmid containing the 4 kb insert was insensitive to this phage. When the plaque assay technique was applied to this strain, a very low number of plaques was observed ($10^1$ to $10^2$ pfu/ml compared with $10^2$/ml when titred against the plasmid-free S. lactis MG1363). However, with each subculture, the titre of phage 712 increased, suggesting the loss of the inserted DNA in pAM401 due to instability. This was confirmed when phage-sensitive transformants were shown to contain the original pAM401 (i.e. with no insert) The instability was observed in S. lactis only. The insert was stably maintained in pAM401 in the E. coli LE392 background.

Figure 12:
FIG. 12 Agarose gel depicting the restriction analysis of the recombinant plasmid pCI816 which confers phage insensitivity on *S. lactis* MG1363 (against phage 712).
  Lanes 1 & 5—Lambda-EcoR1 and EcoR1/HindIII standard digests, respectively.
  Lane 2—pCI829 digested with StuI generating fragments of 33.7 and 6.3 kb
  Lane 3—pCI816 digested with AvaI generating fragments of 10.3 and 6.2 kb. The 10.3 kb product consists of the 6.3 kb StuI fragment of pCI829 and the 4.0 kb AvaI fragment of pSA3.
  Lane 4—pSA3 digested with AvaI generating fragments of 6.2 and 4.0 kb.

The restriction endonucleases StuI generates two fragments of 6.3 kb and 33 kb on pCI829. Using the shotgun cloning approach, the 6.3 kb fragment was cloned into the single NruI site of pSA3 (see FIG. 11) (the 33 kb fragment was too large to be cloned in this manner) and the recombinant plasmid was transformed into E. coli HB101. The cloning strategy is outlined in detail in FIG. 11. The presence of the StuI fragment in pSA3 was demonstrated by performing an AvaI digest of the recombinant plasmid (FIG. 12). AvaI cuts pSA3 into two fragments of 4.0 and 6.2 kb. The NruI insertion site used in the cloning experiment is within the 4.0 kb fragment so the AvaI digest of the hybrid molecule shows a 10.3 kb fragment instead of the 4.0 kb band indicating that the 6.3 kb StuI fragment had indeed inserted into pSA3. The recombinant plasmid was designated pCI816.

pCI816 was transformed into S. lactis MG1363 by electroporation at a frequency of $2.9 \times 10^1/\mu g$ DNA. Transformants containing pCI816 were found to be almost totally insensitive to phage 712 in that there was only interference with the lawn o& cells on the zero and first dilutions in a standard plaque assay where the titre of the phage on its homologous host S. lactis 712 was $7.0 \times 10^8$. When challenged with phage c2 a 50% reduction in plaque size was observed but there was no change on efficiency of plaquing (e.o.p).

Figure 13:
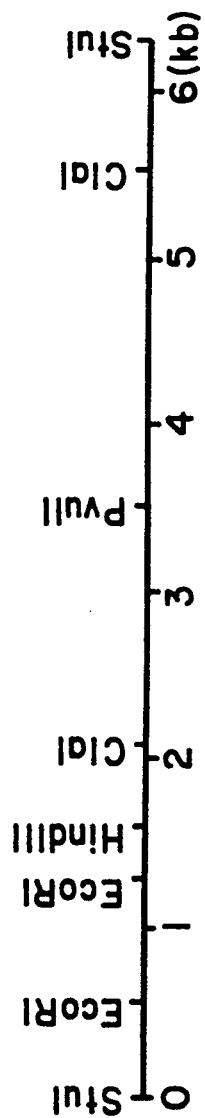
FIG. 13 Detailed restriction map of the cloned 6.3 kb StuI insert from pCI829.

The cloned 6.3 kb StuI fragment from pCI829 encoding phage insensitivity has been restriction mapped in greater detail than pCI829 itself and this is shown in FIG. 13.

Figure 14:
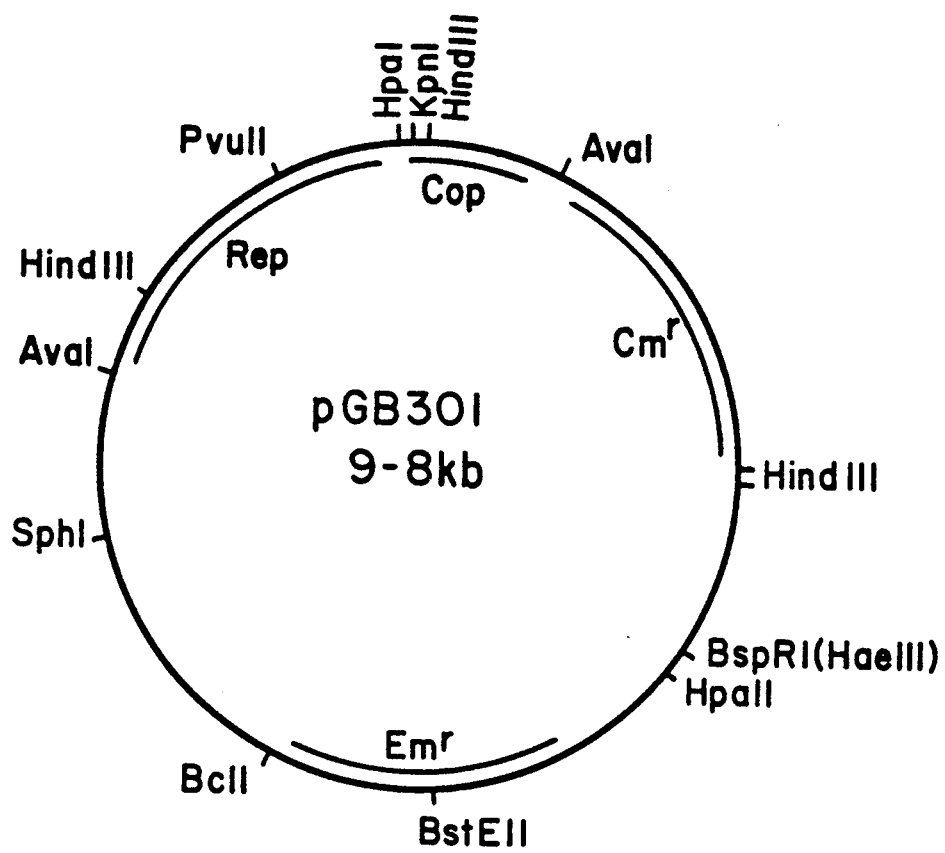
FIG. 14 Restriction map of the streptococcal plasmid cloning vector pGB301. (from Behnke et al.—see ref 35)

The genes encoding phage insensitivity on pCI750 were isolated by inserting BcII restriction fragments of the plasmid into the unique BcII site of pGB301 (FIG. 14). Following ligation, the mix was transformed directly into S. lactis LM0230 and erythromycin and chloramphenicol resistant transformants were isolated from the ligation mix at a frequency of $1.2 \times 10^3/\mu g$ DNA. Transformants were scored for their phage insensitivity by replica plating onto plates overlaid with phage 712 (i.e. only transformants that had acquired phage insensitivity determinants could grow and produce a colony). Of 1800 transformants tested in this manner two were able to grow indicating that they had acquired phage insensitivity determinant(s). The first, designated S. lactis MM113, exhibited reduced sensitivity to phage 712 (unlike strains containing the entire pCI750, strain MM113 was not totally insensitive to this phage) in that the e.o.p. of the phage was reduced by three log cycles and the plaque size was also reduced by about 50%. Phage c2 plagued with a reduced plaque size also but the e.o.p. was only very slightly reduced (by less than one log cycle).

Plasmid profile analysis of strain MM113 revealed the presence of a molecule that co-migrated with pGB301 (FIG. 15) and the absence of any inserts in this plasmid was confirmed by restriction analysis. An erythromycin-sensitive, chloramphenicol-sensitive, plasmid-free isolate of S. lactis MM113 generated by growth at 37° C. still exhibited the reduced phage sensitivity phenotype. These data suggest that the phage insensitivity genes are stabilized by integration into the host chromosome.

Figure 15:
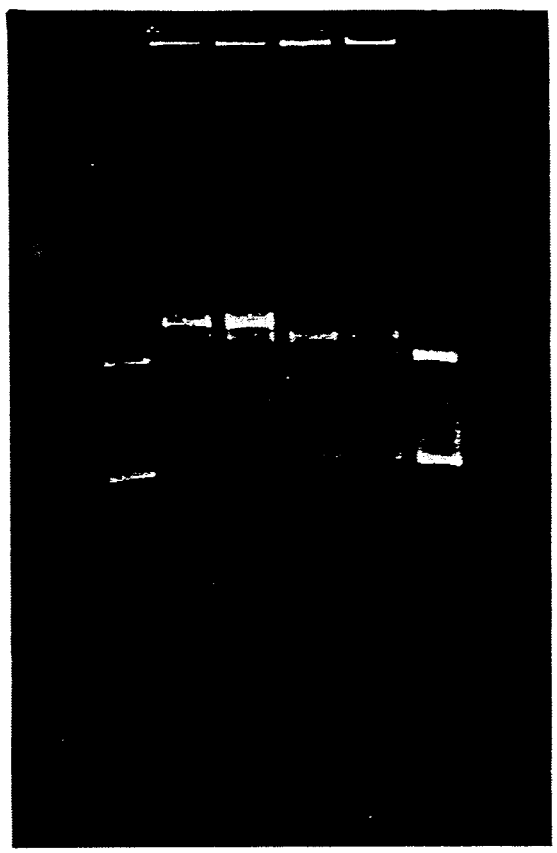
FIG. 15 Agarose gel depicting plasmid profiles of the phage insensitive transformants *S. lactis* MMI13 and *S. lactis* MM1
  Lane 1 & 6—pGB301, the cloning vector (9.8 kb)
  Lane 2 & 3—*S. lactis* MMI containing the recombinant plasmid pMMI (25.5 kb)
  Lane 4 & 5—*S. lactis* MMI13 containing a plasmid of 9.8 kb which co-migrates with pGB301 (i.e. even though the host displays phage insensitivity, there is no inserted DNA in the vector suggesting that the DNA mediating phage insensitivity has inserted into the chromosome).
Figure 16:
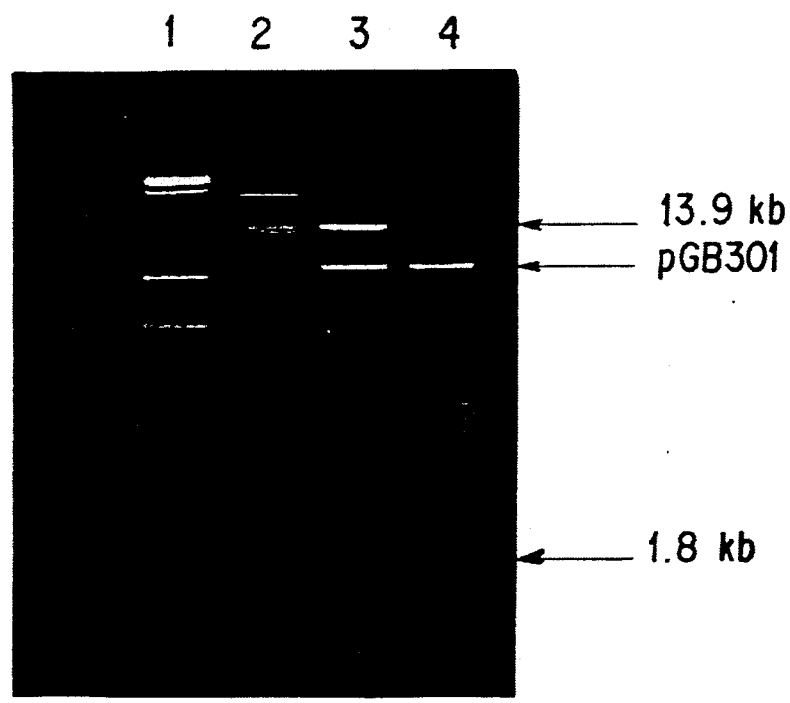
FIG. 16 Agarose gel depicting restriction analysis of the recombinant plasmid pMMl which confers a degree of phage insensitivity on S. lactis LM0230 (against phage 712).

The second transformant capable of growing on the selection plates was designated S. lactis MM1. Phage 712 did not form any plaques on this strain but the cell lawn had a mottled appearance compared with the phage free control. Phage c2 plagued with a reduced plaque size and a very slightly reduced e.o.p. S. lactis MM1 contained a plasmid of 25.5 kb. designated pMM1 (FIG. 15). Restriction analysis of pMM1 showed that two BcII restriction fragments of 13.9 and 1.8 kb had inserted into the unique BcII site of pGB301 (FIG. 16). Curing pMM1 from strain MM1 resulted in reversion to a phage sensitive phenotype indicating that the cloned DNA was responsible for the reduced phage sensitivity phenotype.

The cloned insert from pCI750 (i.e. containing the 13.9 and 1.8 kb BcII fragments) which encodes phage insensitivity was restriction mapped in greater detail that pCI750 itself and this is shown in FIG. 17.

Identification of a bacteriophage insensitive plasmid from S. cremoris UC503

Experience in this laboratory has shown that S. cremoris UC503 displayed a high natural level of phage insensitivity. Mutants showing increased insensitivity to the homologous phage uc503 (i.e. a significant increase in plaque size) were readily isolated either spontaneously or after acriflavin (20 $\mu g$/ml) treatment. Analysis of the plasmid profiles of selected representative mutants showed the consistent loss of a 28 Mdal plasmid, pCI528 (FIG. 18). Furthermore, these mutants were also sensitive to c2 and uc811, phage which were incapable of plaquing on S. lactis UC503 which contains pCI528 (Table 5).

Introduction of the phage insensitivity plasmid pCI528 into S. lactis MG1363

Figure 19:
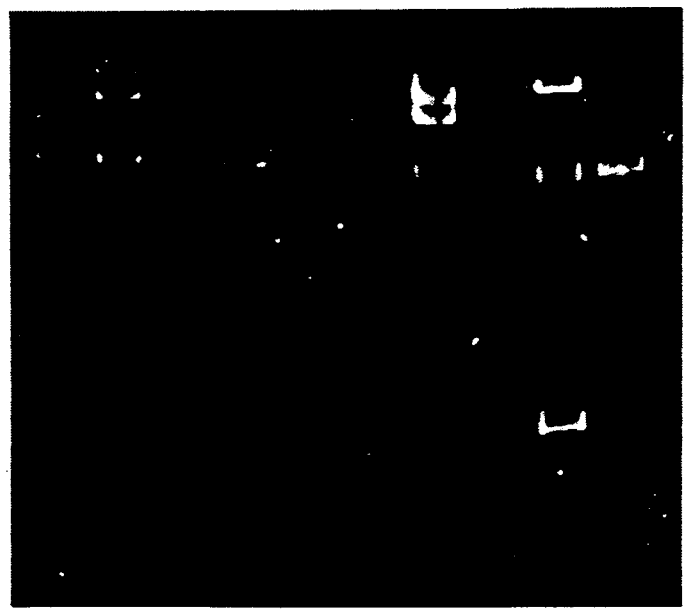

It was not possible to transfer pCI528 from its S. cremoris UC503 host to an S. lactis MG1363 Sm recipient using the conjugative mobilization described earlier for plasmids pCI750 and pCI829. The introduction of the promiscuous plasmid pAMBI as a mobilizing agent (from an S. lactis MG3020 donor) also failed to bring about transfer of pCI528. The alternative approach of using protoplast transformation was applied. Total plasmid DNA from S. cremoris UC503 containing pAMBI was isolated and used to transform S. lactis Sm protoplasts. Transformants were selected on the basis of resistance to erythromycin (Em) encoded by pAMBI and the plasmid profiles of 50 individual isolates were examined. A single isolate, designated UC504, harboured a 28 Mdal plasmid (in addition to pAMBI and two cryptic plasmids from strain UC503) (FIG. 19. lane 4). pAMBI was eliminated from UC504 following heat curing treatments. pCI528 was removed from the presence of the two cryptic plasmids by conjugating it into *S. lactis* MG1299 (i.e. *S. lactis* MG1363 containing pLP712, a Lac/Prt plasmid from *S. lactis* 712). The plasmid profile of a transconjugant, designated UC505, containing both pC1529 and pLP712 is shown in FIG. 19 (lane 7).

Comparison of the phage sensitivity patterns of *S. lactis* strains UC505 and MG1363 Sm

*S. lactis* MG1363 Sm is sensitive to phage 712, c2, m13 and jj50 (Table 6). However, when these phage were titred against UC505 no plaques were formed by any of the phage, even though phages such as m13 had previously been shown to be extremely virulent. Increasing the temperature to 37° C. or 39° C. had minimal or no effect on the insensitivity mechanism.

Examination of the adsorption of phage 712, c2, m13 and jj50 to UC505.

Adsorption tests showed that phages 712, c2, m13 and jj50 were capable of adsorbing to *S. lactis* MG1363 Sm at high efficiency (Table 7). However, the efficiencies of adsorption of the same phage to UC505 were between 35 and 45%. These data suggest that the phage insensitivity mechanism associated with pCI528 is different to those encoded by pCI750 and pCI829 and also to pTR2030 of Klaenhammer's group.

Milk activity tests comparing the ability of *S. lactis* strains MG1299 and UC505 to produce acid in the presence of homologous phage.

Heap-Lawrence milk activity tests were performed to compare the ability of UC505 and MG1299 to produce acid in the presence of virulent phage. The data in Table 8 show that UC505 was capable of surviving of the test in the presence of high titres of phage 712, c2, m13 or jj50, or a cocktail of all four phage with no effect at all on acid producing ability. In contrast, MG1299 was unable to produce acid when exposed to any of the phage combinations.

Identification of the protein products from the cloned 6.3 kb StuI fragment from pCI829

Comparison of the protein products generated by pSA3 and pCI816 (i.e. the recombinant plasmid containing the 6.3 kb StuI fragment from pCI829 and encoding phage insensitivity) in *E. coli* maxicells showed that only one protein of 10 KDa could be attributed to the 6.3 kb insert in the vector plasmid (FIG. 20). This may indicate that this protein is involved in mediating the phage insensitivity encoded by pCI829.

LITERATURE CITED

1. McKay, L. L. and K. A. Baldwin. 1984. Conjugative 40 Mdal plasmid in *Streotococcus lactis* subsp. diacetylactis DRC3 is associated with resistance to nisin and bacteriophage. Appl. Environ. Microbiol. 47:68–74.

2. Klaenhammer, T. R. and R. B. Sanozky, 1985. Conjugal transfer from *Streptococcus lactis* ME2 of plasmids encoding phage resistance, nisin resistance and lactose fermenting ability; evidence for a high-frequency conjugative plasmid responsible for abortive infection of virulent bacteriophage. J. Gen. Microbiol. 131:1531–1541.

3. Steenson, L. R. and T. R. Klaenhammer. 1985. *Streptococcus cremoris* M12R transconjugants carrying the conjugal plasmid pTR2030 are insensitive to attack by lytic bacteriophages. Appl. Environ. Microbiol. 50:851–858.

4. Sing, W. D. and T. R. Klaenhammer. 1986. Conjugal transfer of bacteriophage resistance determinants on pTR2030 into *Streptococcus cremoris* strains. Appl. Environ. Microbiol. 51:1264–1271.

5. Jarvis, A. W. and T. R. Klaenhammer. 1986. Bacteriophage resistance conferred on lactic streptococci by the conjugative plasmid pTR2030: effects on small isometric-, large isometric-, and prolate-headed phages. Appl. Environ. Microbiol. 51:1272–1277.

6. Jarvis, A. W. and T. R. Klaenhammer. 1987. Bacteriophage resistance plasmid pTR2030 inhibits infection on rlt temperate bacteriophage but not induction of rlt prophage in *Streptococcus cremoris*. Appl. Environ. Microbiol. 53:385–389.

7. Sanders, M. E., P. J. Leonhard, W. D. Sing and T. R. Klaenhammer. 1986. Conjugal strategy for construction of fast acid producing, bacteriophage-resistant lactic streptococci for use in dairy fermentations. Appl. Environ. Microbiol. 52:1001–1007.

8. Terzaghi, B. E. and W. E. Sandine. 1975. Improved medium for lactic streptococci and their bacteriophage. Appl. Environ. Microbiol. 29:807–813.

9. Hill, C., C. Daly and G. F. Fitzgerald. 1985. Conjugative transfer of the transposon Tn919 to lactic acid bacteria. FEMS Microbiol. Lett. 30:115–119.

10. McKay L. L., K. A. Baldwin and P. M. Walsh. 1980. Conjugal transfer of genetic information in group N. streptococci. Appl. Environ. Microbiol. 40:84–91.

11. McKay, L. L., K. A. Baldwin and E. A. Zottola. 1972. Loss of lactose metabolism in *S. Lactis* C2. Appl. Microbiol. 23:1090–1096.

12. Gasson, M. J. and P. H. Anderson, 1985. High copy number plasmid vectors for use in lactic streptococci. FEMS Microbiol. Lett. 30:193–196.

13. Heap, H. A. and R. C. Lawrence, 1986. The selection of starter strains for cheese-making. N.Z.J. Dairy Sci. Technol. 11:16–22.

14. Anderson, D. G. and L. L. McKay, 1983. Simple and rapid method for isolating large plasmid DNA from lactic streptococci. Appl. Environ. Microbiol. 46:549–552.

15. Maniatis, T., E. F. Fritsch and J. Sambrook, 1982. Molecular cloning: a laboratory manual. Cold Spring Laboratory, Cold Spring Harbor, N.Y.

16. Coveney, J., G. F. Fitzgerald and C. Daly, 1987. Detailed characterization and comparison of four lactic striptococcal bacteriophage based on morphology, restriction mapping, DNA homology and structural protein analysis,. Appl. Environ. Microbiol. 53: 1539–1447.

17. Southern, E. M. 1975. Detection of specific sequences among DNA fragments separated by gel electrophoresis. J. Mol. Biol. 98:5503–5517.

18. Wirth, R., F. Y. An and D. R. Clewell. 1986. Highly efficient protoplast transformation system for *Streptococcus faecalis* and a new *Escherichia coli*—*S. faecalis* shuttle vector, J. Bacteriol. 165:831–836.

19. Sanders, M. E. and T. R. Klaenhammer. 1983. Characterization of phage sensitive mutants from a phage insensitive strain of *Streptococcus lactis*: evidence for a plasmid determinant that prevents phage adsorption. Appl. Environ. Microbiol. 46:1125-1133.

20. de Vos, W. M., H. M. Underwood and F. L. Davies. 1984. Plasmid encoded bacteriophage resistance in Streotococcus cremoris SK11. FEMS Microbiol Lett. 23:175-178.

21. Chopin, A., M. C. Chopin, A. Moillo-Batt and P. Langella. 1984. Two plasmid determined restriction-modification systems in Streotococcus lactis. Plasmid 11:260-263.

22. Sanders, M. E and T. R. Klaenhammer, 1981. Evidence for plasmid linkage of restriction and modification in Streotococcus cremoris KH. Appl. Environ. Microbiol. 42:944-950.

23. Wetzel, A., H. Neve, A. Geis and M. Teuber. 1986. Transfer of plasmid mediated phage resistance in lactic acid streptococci. Chem. Mikrobiol. Technol. Lebensm. 10:86-89.

24. Klaenhammer, T. R. and R. B. Sanozky-Dawes. 1986. A conjugal plasmid which confers phage restriction and modification activities to lactic streptococci. Abstract 222 from Second ASM Conference on Streptococcal Genetics, 21-24 May, Miami Beach, Fla. U.S.A.

25. Daly, C. and G. F. Fitzgerald. 1987. Mechanisms of bacteriophage insensitivity in the lactic streptococci. In Streptococcal Genetics (Ferretti, J. J. and R. C. Curtiss III, eds.) American Society for Microbiology, Washington D.C. U.S.A.

26. Klaenhammer, T. R. 1984. Interactions of bacteriophages with lactic streptococci. Adv. Appl. Microbiol. 30:1-29.

27. Steenson, L. R. and T. R. Klaenhammer. 1986. Plasmid heterogeneity in Streotococcus cremoris M12R: Effects on proteolytic activity and host dependent phage replication. J. Dairy Sci. 69:2227-2236.

28. Geis, A. H. and M. Teuber. 1987. Plasmid dependent bacteriophage resistance in lactic acid streptococci. Abstract from C.E.C. Meeting 'Culture Collection and Genetic Engineering of Microorganisms' Ioannina, Greece. pp. 33. Commission of the European Communities.

29. Davies, S. L. & M. G. Gasson, 1984. Bacteriophages of Dairy Lactic Acid Bacteria, in Advances in Microbiology and Biochemistry of Cheese and Fermented Milk. (Davies, F. L. & B. A. Law, eds.) pp 127-151, Elsevier Applied Science Publishers, London.

30. Macrina, F. L., J. A. Tobian, K. R. Jones, R. P. Evans and D. B. Clewell. 1982. A cloning vector able to replicate in Escherichia coli and Streotococcus sanguis. Gene. 19:345-353.

31. Mandel. M. and A. Higa. 1970. Calcium-dependent bacteriophage DNA infection. J. Mol. Biol. 53:159-162.

32. Kondo. J. K. and L. L. McKay. 1984. Plasmid transformation of Streptococcus lactis protoplasts: optimization and use in molecular cloning. Appl. Environ. Microbiol. 48:252-259.

33. Sancar, A., A. M. Hack and W. D. Rupp, 1979. Simple method for identification of plasmid-coded proteins. J. Bacteriol. 137:692-693.

34. Dao, M. J. and J. J. Ferretti. 1985. Streptococcus-Escherichia coli shuttle vector pSA3 and its use in the cloning of streptococcal genes. Appl. Environ. Microbiol. 49:115-119.

35. Behnke, D., M. S. Gilmore and J. J. Ferretti. 1981. Plasmid pBG301, a new multiple resistant streptococcal cloning vehicle and its use in cloning of the gentamycin/kanamycin resistance determinant. Mol. Gen. Genet. 182:414-421.

TABLE 1

Conjugative transfer of Lac and phage insensitivity

| Donor | Recipient | Lac+ Transconjugants Frequency/Recipient | % phage 712 insensitive |
|---|---|---|---|
| S. Cremoris UC653 | S. lactis MG1363 Sm | $3.3 \times 10^{-7}$ | EG 70 (AB001) |
| S. lactis BA2 | S. lactis MG1363 Sm | $1.43 \times 10^{-4}$ | 11 (AC001) |
| S. lactis AB001 | S. lactis LM0230 | $7.6 \times 10^{-9}$ | 15 |
| S. lactis AC001 | S. lactis LM0230 | $1.8 \times 10^{-5}$ | 60 |

TABLE 2

Conjugative transfer of Lac and phage insensitivity

| Donor | Recipient | Lac+ Transconjugants Frequency/Recipient | % phage 712 insensitive | Transconjugant Designation |
|---|---|---|---|---|
| S. lactis AB001 | S. lactis LM2306 | $4.0 \times 10^{-7}$ | 75.0 | |
| S. lactis AB002 | S. lactis LM2306 | $3.7 \times 10^{-3}$ | 91.7 | |
| S. cremoris UC653 | S. lactis MMS366 | $3.0 \times 10^{-7}$ | 100 | (a) MM20 (b) MM21 |

TABLE 3

EFFECT OF TEMPERATURE ON REPLICATION OF SELECTED PHAGE ON S. LACTIS MG1363 SM AND BACTERIOPHAGE INSENSITIVE DERIVATIVES (EOP VALUES).

| | PHAGE | | | | | | | | |
|---|---|---|---|---|---|---|---|---|---|
| TEMP | 712 | C2 | ML3 | EB1 | STL5 | SK1 | 712 | C2 | ML3 |
| | STRAIN | | | | | | | | |
| | S. LACTIS MG1363 SM | | | | | | S. LACTIS AC001 | | |
| 21° C. | 1.0 | 1.0 | 1.0 | 1.0 | 1.0 | 1.0 | 0 | 0 | 0 |
| 30° C. | 1.0 | 1.0 | 1.0 | 1.0 | 1.0 | 1.0 | 0 | $5 \times 10^{-2}$ | 1.0 |

TABLE 3-continued

EFFECT OF TEMPERATURE ON REPLICATION OF SELECTED PHAGE ON
S. LACTIS MG1363 SM AND BACTERIOPHAGE INSENSITIVE
DERIVATIVES (EOP VALUES).

| TEMP | PHAGE | | | | | | | | |
|---|---|---|---|---|---|---|---|---|---|
| | 712 | C2 | ML3 | EB1 | STL5 | SK1 | 712 | C2 | ML3 |
| 37° C. | ND | 1.0 | 1.0 | 1.0 | 1.0 | 1.0 | 0 | $1 \times 10^{-2}$ | 1.0 |
| 40° C. | ND | 1.0 | 1.0 | ND | ND | ND | ND | $2 \times 10^{-1}$ | 1.0 |
| | S. LACTIS AB001 | | | | | | S. LACTIS AC003 | | |
| 21° C. | 0 | 0 | 0 | $3 \times 10^{-6}$ | $5 \times 10^{-3}$ | 0 | 0 | 0 | 0 |
| 30° C. | 0 | $2 \times 10^{-2}$ | $5 \times 10^{-1}$ | $9 \times 10^{-3}$ | $8 \times 10^{-3}$ | 0 | 0 | $1 \times 10^{-7}$ | $2 \times 10^{-3}$ |
| 37° C. | 0 | $2 \times 10^{-4}$ | $7 \times 10^{-1}$ | $6 \times 10^{-4}$ | $2 \times 10^{-3}$ | 0 | 0 | $1 \times 10^{-5}$ | $3 \times 10^{-1}$ |
| 40° C. | ND | $7 \times 10^{-1}$ | $4 \times 10^{-1}$ | ND | ND | ND | ND | $9 \times 10^{-4}$ | $6 \times 10^{-1}$ |

TABLE 4

Transfer of the pCI750 and pCI829-associated phage
insensitivity mechanism(s) to selected strains of lactic
streptococci.

| Donor | Recipient | Lac+ transconjugants Frequency/ Recipient | % insensitive to homologous phage |
|---|---|---|---|
| S. lactis AB002 | S. lactis SK3 Lac− Tc ® | $2.0 \times 10^{-3}$ | 88 |
| | S. lactis subsp. diacetylactis 18-16 Lac− Tc ® | $1.5 \times 10^{-4}$ | 50 |
| | S. cremoris UC411 Lac− Fus ® | $1.5 \times 10^{-3}$ | 94 |
| S. lactis AC003 | S. lactis SK3 Lac− Tc ® | $3.0 \times 10^{-3}$ | 83 |
| | S. lactis subsp. diacetylactis 18-16 Lac− Tc ® | $5.0 \times 10^{-5}$ | 83 |
| | S. cremoris UC411 Lac− Fus ® | $6.0 \times 10^{-4}$ | 50 |

TABLE 5

Data showing increased phage sensitivity of S.
cremoris UC563 (ie. cured of the phage insensitivity
plasmid pCI528) compared to the parent S. cremoris
UC503 (containing pCI528).

Host

| | S. cremoris UC503 | | S. cremoris UC563 | |
|---|---|---|---|---|
| Phage | pfu/ml | plaque size (mm) | pfu/ml | plaque size (mm) |
| c2 | 0 | 0 | $3 \times 10^3$ | <1.55 |
| uc811 | 0 | 0 | $1 \times 10^2$ | <1 |

TABLE 6

Comparison of the sensitivity of S. lactis MG1363
(plasmid-free) and S. lactis UC505 (containing the phage
insensitivity plasmid pCI528) to selected virulent phage at
30, 37 and 39° C.

| | pfu/ml at different temperatures (°C.) | | | | | |
|---|---|---|---|---|---|---|
| | S. lactis MG1363 | | | S. lactis UC505 | | |
| Phage | 30 | 37 | 39 | 30 | 37 | 39 |
| 712 | $2 \times 10^9$ | $3 \times 10^8$ | $6 \times 10^8$ | 0 | 0 | 0 |
| jj50 | $2 \times 10^6$ | $2 \times 10^6$ | $3 \times 10^6$ | 0 | 0 | 0 |
| c2 | $4 \times 10^8$ | $7 \times 10^8$ | $3 \times 10^8$ | 0 | 0 | 0 |
| m13 | $1 \times 10^{10}$ | $>10^{10}$ | $>10^{10}$ | 0 | 0 | 0 |

TABLE 7

Comparison of the efficiency of adsorption of phages to
S. lactis MG1363 and S. lactis UC505 (containing pCI528)

| | % adsorption | |
|---|---|---|
| Phage | S. lactis MG1363 | S. lactis UC505 |
| 712 | 97.46 | 37.31 |
| jj50 | 94.91 | 40.98 |
| c2 | 94.53 | 45.34 |
| m13 | 97.64 | 36 |

TABLE 8

Comparison of the ability of S. lactis MG1299 (containing pLP712) and S. lactis UC503
(containing pLP712 and pCI528) to reduce the pH of milk in the presence of phages 712,
jj50, c2 and m13 or a cocktail of all four using the Heap-Lawrence Milk Activity Test (13).

| Phage/ cycle | S. lactis MG1299 | | | | | | S. lactis UC505 | | | | | |
|---|---|---|---|---|---|---|---|---|---|---|---|---|
| | control* | 712 | jj50 | c2 | m13 | cocktail | control* | 712 | jj50 | c2 | m13 | cocktail |
| 1 | 4.94 | 6.47 | 6.49 | 6.48 | 6.48 | 6.48 | 4.94 | 4.87 | 4.89 | 4.88 | 4.88 | 4.93 |
| 2 | 5.06 | 6.49 | 6.49 | 6.49 | 6.49 | 6.49 | 5.09 | 5.02 | 5.07 | 5.05 | 5.02 | 5.06 |
| 3 | 4.84 | 6.55 | 6.55 | 5.75 | 6.53 | 6.55 | 5.91 | 4.93 | 5.87 | 4.86 | 4.88 | 4.92 |
| 4 | 5.17 | 6.48 | 6.48 | 6.49 | 6.49 | 6.49 | 5.13 | 5.10 | 5.12 | 5.11 | 5.10 | 5.19 |
| 5 | 5.06 | 6.48 | 6.48 | 6.48 | 6.48 | 6.48 | 5.19 | 5.18 | 5.18 | 5.15 | 5.16 | 5.17 |
| 6 | 4.96 | 6.40 | 6.40 | 6.43 | 6.44 | 6.42 | 5.52 | 4.97 | 4.96 | 4.95 | 5.94 | 4.96 |
| 7 | 5.08 | 6.47 | 6.47 | 6.48 | 6.44 | 6.44 | 5.13 | 5.07 | 5.06 | 5.08 | 5.10 | 5.08 |
| 8 | 5.03 | 6.41 | 6.41 | 6.41 | 6.41 | 6.41 | 5.13 | 5.09 | 5.08 | 5.07 | 5.08 | 5.06 |
| 9 | 4.95 | 6.33 | 6.33 | 6.36 | 6.35 | 6.33 | 5.09 | 5.09 | 5.07 | 5.03 | 5.05 | 5.06 |
| 10 | 5.06 | 6.47 | 6.47 | 6.46 | 6.46 | 6.47 | 5.08 | 5.04 | 5.03 | 5.05 | 5.04 | 5.04 |
| 11 | 5.06 | 6.48 | 6.48 | 6.47 | 6.47 | 6.45 | 5.17 | 5.15 | 5.11 | 5.60 | 5.09 | 5.14 |
| 12 | 5.20 | 6.49 | 6.49 | 6.47 | 6.48 | 6.49 | 5.27 | 5.23 | 5.21 | 5.21 | 5.24 | 5.25 |

*no phage added to the milk
0.1 ml of the appropriate phage suspension (each at approximately 10 pfu/ml) was added to cycle 1. In subsequent cycles (2-12)
0.5 ml of phage suspension and 0.05 of whey from the previous cycle were added.

TABLE 9

Effect of the pCI750 and pCI829 encoded mechanisms
individually and together on the plaque size of phage 712
and c2

| | plaque size of phage (mm) | |
|---|---|---|
| Host (plasmid) | 712 | c2 |
| S. lactis MG1363 (plasmid-free) | 0 | 3 |
| S. lactis AB001 (pCI750) | 0 | 1-1.5 |
| S. lactis AC001 (pCI829) | 0 | 1-1.5 |

TABLE 9-continued

Effect of the pCI750 and pCI829 encoded mechanisms individually and together on the plaque size of phage 712 and c2

| Host (plasmid) | plaque size of phage (mm) | |
|---|---|---|
| | 712 | c2 |
| S. lactis AC003 (pCI751 + pCI829) | 0 | 0 |

We claim:

1. A plasmid having the identifying characteristics of a plasmid selected from the group consisting of:

plasmid pCI750 as deposited in bacterial strain S. lactis AB001 at the National Collection of Industrial Bacteria, Aberdeen, Scotland, under accession no. 12261, plasmid pCI777 as deposited in bacterial strain S. lactis AB002 at the National Collection of Industrial Bacteria, Aberdeen, Scotland, under accession no. 12262, and plasmid pCI528 as deposited in bacterial strain, S. lactis AB002 at the National Collection of Industrial Bacteria, Aberdeen, Scotland, under accession no. 12478.

2. A plasmid as claimed in claim 5 is isolated form.

3. Bacterial hosts comprising one or more plasmids of claim 5.

4. Bacterial hosts according to claim 3 which are Group N Streptococci.

5. Bacterial hosts as claimed in claim 4 in isolated form.

6. A method of conferring phage insensitivity on lactic acid streptococci in a diary fermentation starter culture comprising introducing into the streptococci a plasmid according to claim 5.

* * * * *

UNITED STATES PATENT AND TRADEMARK OFFICE
CERTIFICATE OF CORRECTION

PATENT NO. : 5,019,506

DATED : May 28, 1991

INVENTOR(S) : Charles Daly; Gerald F. Fitzgerald; Aidan Coffey; Veronica A. Costello; Maeve C. Murphy; and Andreas Baumgartner It is certified that error appears in the above identified patent and that said Letters Patent is hereby corrected as shown below:

Column 28, line 7, change "5" to --1--.

Column 28, line 9, change "5" to --1--.

Column 28, line 17, change "5" to --1--.

Signed and Sealed this

Fifth Day of January, 1993

Attest:

DOUGLAS B. COMER

Attesting Officer

Acting Commissioner of Patents and Trademarks